United States Patent
Takeuchi et al.

(10) Patent No.: US 11,035,843 B2
(45) Date of Patent: Jun. 15, 2021

(54) METHOD FOR EVALUATING ABILITY OF CELLS TO GROW INTO SHEET

(71) Applicant: TERUMO KABUSHIKI KAISHA, Tokyo (JP)

(72) Inventors: Ryohei Takeuchi, Kanagawa (JP); Kouichirou Yori, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 778 days.

(21) Appl. No.: 15/717,325

(22) Filed: Sep. 27, 2017

(65) Prior Publication Data

US 2018/0067099 A1 Mar. 8, 2018

Related U.S. Application Data

(63) Continuation of application No. PCT/JP2016/060010, filed on Mar. 29, 2016.

(30) Foreign Application Priority Data

Mar. 30, 2015 (JP) .............................. JP2015-069588

(51) Int. Cl.
*G01N 33/50* (2006.01)
*G01N 33/483* (2006.01)
*G01N 27/04* (2006.01)
*G01N 27/02* (2006.01)

(52) U.S. Cl.
CPC ....... *G01N 33/4833* (2013.01); *G01N 27/041* (2013.01); *G01N 27/026* (2013.01)

(58) Field of Classification Search
CPC . G01N 33/4833; G01N 27/041; G01N 27/026
See application file for complete search history.

(56) References Cited

U.S. PATENT DOCUMENTS

| | | | |
|---|---|---|---|
| 5,187,096 A | 2/1993 | Giaever et al. | |
| 2007/0212773 A1* | 9/2007 | Fujii | C12M 41/36 435/287.1 |
| 2008/0099878 A1* | 5/2008 | Yukawa | G11C 13/004 257/530 |
| 2014/0186941 A1 | 7/2014 | Zhou et al. | |

FOREIGN PATENT DOCUMENTS

| | | |
|---|---|---|
| JP | 2007-215473 A | 8/2007 |
| JP | 2007-528755 A | 10/2007 |
| JP | 2012-152188 A | 8/2012 |
| JP | 2012-152189 A | 8/2012 |
| WO | WO 2012-169493 A1 | 12/2012 |
| WO | WO 2014-002271 A1 | 1/2014 |

OTHER PUBLICATIONS

English machine translation of WO 2014/002271 A1 obtained on Jul. 12, 2020.*
Office Action (Notification of Reasons for Refusal) dated Sep. 29, 2017, by the Japanese Patent Office in corresponding Japanese Patent Application No. 2017-509995 and English translation of the Office Action. (7 pages).
Notification of Transmittal of Translation of the International Preliminary Report on Patentability (Forms PCT/IB/338 and PCT/IB/373) and the Written Opinion of the International Searching Authority (Form PCT/ISA/237) dated Oct. 3, 2017, in the corresponding International Application No. PCT/JP2016/060010. (11 pages).
Nori, "ECIS (Electrical cell-substrate impedance sensing system)", BME, 2001, vol. 15, No. 2, pp. 54-60, (9 Total pages).
ECIS Product Guide, Applied BioPhysics, May 2014, (36 pages).
Fahey et al., "Secretory Component Production by Polarized Epithelial Cells from the Human Female Reproductive Tract," Immunological Investigations, (May 1998), vol. 27, No. 3, pp. 167-180.
Kubota et al., "Transplantable Retinal Pigment Epithelial Cell Sheets for Tissue Engineering," Biomaterials, (Jul. 2006), vol. 27, Issue 19, pp. 3639-3644.
Okanlawon et al., "Effect of Chloroquine on the Formation of Tight Junctions in Cultured Immature Rat Sertoli Cells," Journal of Andrology, (May/Jun. 1996), vol. 17, No. 3, pp. 249-255.
Szulcek et al., "Electric Cell-substrate Impedance Sensing for the Quantification of Endothelial Proliferation, Barrier Function, and Motility," Journal of Visualized Experiments, (Mar. 28, 2014), No. 85, e51300, pp. 1-12.
Wegener et al., "Automated multi-well Device to Measure Transepithelial Electrical Resistances under Physiological Conditions," BioTechniques, (Oct. 2004), vol. 37, No. 4, pp. 590-597.
The extended European Search Report dated Jan. 7, 2019, by the European Patent Office in corresponding European Patent Application No. 16772778.3-1003. (9 pages).
International Search Report (PCT/ISA/210) dated Jun. 21, 2016, by the Japanese Patent Office as the International Searching Authority for International Application No. PCT/JP2016/060010.
Written Opinion (PCT/ISA/237) dated Jun. 21, 2016, by the Japanese Patent Office as the International Searching Authority for International Application No. PCT/JP2016/060010.

* cited by examiner

*Primary Examiner* — Russell S Negin
(74) *Attorney, Agent, or Firm* — Buchanan Ingersoll & Rooney PC

(57) ABSTRACT

A method for evaluating the ability of cells to grow into a sheet includes (1) a step of examining cell cultures growing into a sheet to determine their impedance and/or electrical resistance or numerical values relating thereto; (2) a step of comparing the numerical values determined by Step (1) with reference values; and (3) a step of judging, based on the results of comparison obtained in Step (2), the ability of cells to grow into a sheet.

20 Claims, 6 Drawing Sheets

METHOD FOR EVALUATING ABILITY OF CELLS TO GROW INTO SHEET

CROSS-REFERENCES TO RELATED APPLICATIONS

This application is a continuation of International Application No. PCT/JP2016/060010 filed on Mar. 29, 2016, and claims the benefit of Japanese Application No. JP2015-069588 filed on Mar. 30, 2015, the entire content of each of which is incorporated herein by reference.

TECHNICAL FIELD

The present invention relates to a method and system for evaluating the ability of cells to grow into a sheet.

BACKGROUND ART

Attempts are being made in recent years to transplant a variety of cells for the purpose of healing damaged tissues. Such attempts are intended to heal heart tissues damaged by ischemic heart disease such as cardiac angina and cardiac infarction. As discussed, for example, in Haraguchi et al., Stem Cells Transl Med. 2012 February; 1(2):136-41, cells for transplantation include fetal cardiocytes, skeletal myoblasts, mesenchymal stem cells, cardiac stem cells, ES cells, and the like. JP-T-2007-528755 describes an attempt directed partly to the development of a cell structure formed by means of a scaffold or a cell culture in sheet form (which is an aggregate of cells resembling a sheet).

Therapeutic application of a cell culture in sheet form is under study for the healing of skin damaged by burns with a sheet-shaped cell culture of skin, the healing of damaged cornea with a sheet-shaped cell culture of corneal skin, and the healing of esophageal carcinoma after endoscopic resection with a sheet-shaped cell culture of oral mucosa.

The application of a cell culture to clinical practice requires that the cell culture should have adequate applicability, effectiveness, safety, storage life, and transportability. This leads to the necessity of establishing an index for an optimal method of production and an index for quality control (such as measurement of strength of the sheet-shaped cell culture). Evaluation of the sheet-shaped cell culture in terms of strength or the like may be accomplished by any one the methods disclosed in JP-A-2012-152188 and JP-A-2012-152189. The former describes the method for determining the concentration (or change thereof) of non-adhering cells in the liquid culture medium being used for sheet-forming cultivation, thereby judging the extent to which the sheet-shaped cell culture has grown. The latter describes the method for calculating the portion of the sheet-forming cells sticking to the culture container, thereby judging the formation of the sheet-shaped cell culture.

SUMMARY

During their research into sheet-shaped cell cultures, the present inventors found that cultivation under the same conditions gives rise to sheet-shaped cell cultures varying in properties. For example, some samples break, losing the sheet shape, at the time of detaching from the culture substrate, and some samples detach spontaneously from the culture substrate before the end of cultivation. With this in mind, the present inventors continued their research assuming that an efficient production of sheet-shaped cell cultures would be possible if there is a way to predict whether or not cells form normal sheet-shaped cell cultures under ordinary conditions. From their research, they found that it is possible to discriminate between cells capable of forming normal sheet-shaped cell cultures and other cells based on some numerical values, such as electrical resistance, of the cell culture which are measured during cultivation of cells to form the sheet-shaped cell cultures. This finding led to the following exemplary embodiments.

<1> A method for evaluating the ability of cells to grow into a sheet, including:
(1) a step of examining cell cultures growing into a sheet to determine their impedance and/or electrical resistance or numerical values relating thereto;
(2) a step of comparing the numerical values determined by Step (1) with reference values; and
(3) a step of judging, based on the results of comparison obtained in Step (2), the ability of cells to grow into a sheet.

<2> A method for producing a sheet-shaped cell culture, including:
(1) a step of examining cell cultures growing into a sheet to determine their impedance and/or electrical resistance or numerical values relating thereto;
(2) a step of comparing the numerical values determined by Step (1) with reference values;
(3) a step of judging, based on the results of comparison obtained in Step (2), the ability of cells to grow into a sheet; and
(4) a step of controlling, based on the result of judgment obtained in Step (3), a process of producing the sheet-shaped cell culture.

<3> The method defined in Paragraph <1> or <2> above, in which the determination of impedance and/or electrical resistance is performed periodically in Step (1).

<4> The method defined in any of Paragraphs <1> to <3> above, in which Step (1) further includes determination of voltage phase relative to current phase.

<5> The method defined in any of Paragraphs <1> to <4> above, in which the determination of impedance in Step (1) is performed at two or more frequencies.

<6> The method defined in any of Paragraphs <1> to <5> above, in which the numerical values relating to impedance are parameters selected from a group consisting of electrical resistance, capacitance, Rb, α, Rb/α, and Cm of the cell culture and also selected from a group consisting of peak values, times to peak, and slopes to peak of the parameters.

<7> The method defined in any of Paragraphs <1> to <6> above, in which cells are judged to be low in ability to grow into a sheet if the electrical resistance determined in Step (3) is equal to or smaller than the reference value.

<8> The method defined in Paragraph <6> or <7> above, in which cells are judged to be low in ability to grow into a sheet if the values of Rb, α, and Rb/α determined in Step (3) are equal to or smaller than the reference values.

<9> The method defined in Paragraph <6> or <7> above, in which cells are judged to be adequate or excessive in ability to grow into a sheet if the values of Rb, α, and Rb/α determined in Step (3) are equal to or larger than the reference values.

<10> The method defined in Paragraph <6> above, in which cells are judged to be low in ability to grow into a sheet if the numerical values selected from a group consisting of the peak value of electrical resistance, the peak value of Rb, and the slope to peak of Rb determined in Step (3) are equal to or smaller than the reference values, and/or if the numerical values selected from a group consisting of the time to peak of electrical resistance and the time to peak of Rb are equal to or larger than the reference values.

<11> The method defined in Paragraph <6> above, in which cells are judged to be adequate in ability to grow into a sheet if, in Step (3), the numerical values selected from a group consisting of the time to peak of electrical resistance and the time to peak of Rb are equal to or smaller than the reference values and the numerical values selected from a group consisting of the peak value of Rb/α and the slope to peak of Rb/α are equal to or smaller than the reference values, and/or if the numerical values selected from the group consisting of the time to peak of electrical resistance and the time to peak of Rb are equal to or smaller than the reference values and the time to peak of Rb/α is equal to or longer than the reference value.

<12> The method defined in Paragraph <6> above, in which cells are judged to have excessive ability to grow into a sheet if, in Step (3), the numerical values selected from a group consisting of the peak value of Rb/α and the slope to peak of Rb/α are equal to or larger than the reference values, and/or if the time to peak of Rb/α is equal to or shorter than the reference value.

<13> A system for evaluating the ability of cells to grow into a sheet, including: a container for cultivation to grow cells into a sheet; and a measuring apparatus to determine impedance and/or electrical resistance of the cell culture in the container.

These methods are intended to evaluate the ability of cells to grow into a sheet. The results of such evaluation permit one to control the process of producing the sheet-shaped cell cultures according to the ability of cells to grow into a sheet. This leads to efficient production of sheet-shaped cell cultures.

BRIEF DESCRIPTION OF THE DRAWING FIGURES

DETAILED DESCRIPTION

Figure 1:
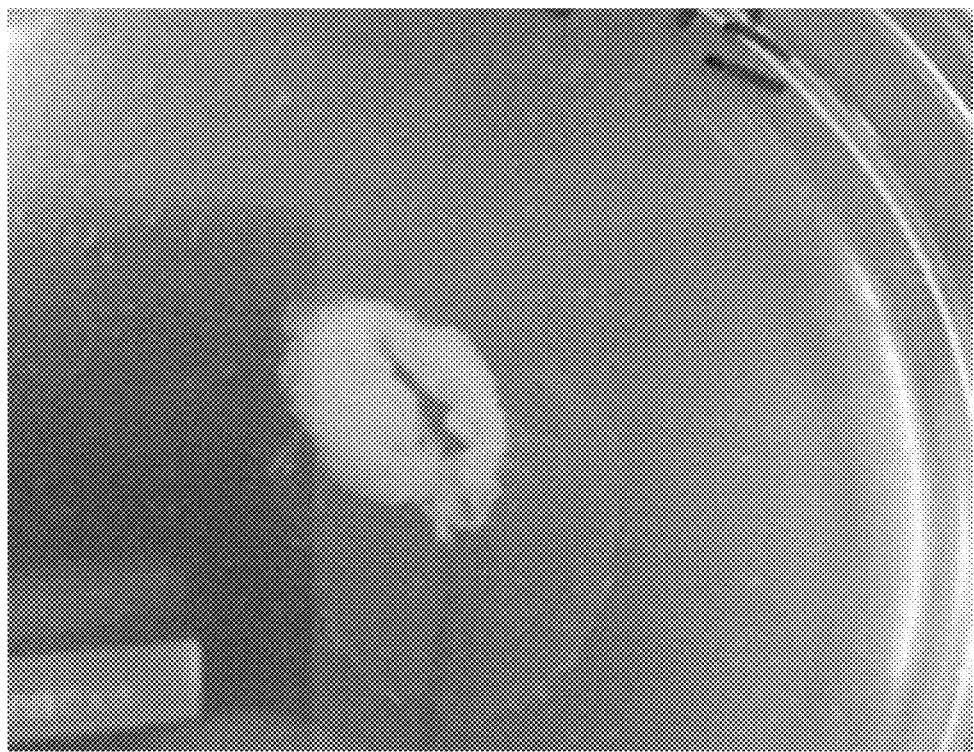
FIG. 1 is a photograph depicting the appearance of a detached sheet.

All the technical and scientific terms used in this specification have the same meaning as ordinarily understood by those who are skilled in the art unless otherwise specifically defined herein.

One aspect of the present disclosure relates to a method for evaluating the ability of cells to grow into a sheet, which includes:

(1) a step of examining cell cultures growing into a sheet to determine their impedance and/or electrical resistance or numerical values relating thereto;

(2) a step of comparing the numerical values determined by Step (1) with reference values; and (3) a step of judging, based on the results of comparison obtained in Step (2), the ability of cells to grow into a sheet. This method will occasionally be abbreviated as "method for evaluation of sheet-forming ability" hereinafter.

The term "ability of cells to grow into a sheet" used in the present disclosure denotes the ability of cells to form a sheet-shaped cell culture. The term "sheet-shaped cell culture" used herein denotes something in sheet form which is composed of cells binding together. It is considered important that cells should be able to bind together and bind themselves to the culture substrate so that cells form a sheet-shaped cell culture, although there is no specific reliable theory. Consequently, the sheet-forming ability may be defined as the general ability of cells to grow into a sheet which includes the ability of cells to bind together and bind themselves to the culture substrate.

The sheet-shaped cell culture typically consists of one cell layer; however, it also includes those which are composed of two or more cell layers placed one over another. Cells constituting the sheet-shaped cell culture may bind together directly and/or indirectly. The direct binding may permit the presence of an intermediate such as adhesion molecules. The indirect binding needs an intermediate placed between cells. The intermediate substance is not specifically restricted so long as it is capable of physically (or mechanically) binding cells together. It includes, for example, an extracellular substrate. The intermediate substance should preferably be one which is derived from cells, particularly one which is derived from cells constituting the sheet-shaped cell culture. Cells should join together at least physically or mechanically; cells may also join together functionally. e.g., chemically or electrically. The sheet-shaped cell culture may exist in the form sticking to or free (detached) from the culture substrate. The latter form, which is typical, will occasionally be called an isolated or free sheet-shaped cell culture hereinafter.

The term "sheet-forming cultivation" used in the present disclosure denotes a manner of cultivation in which cells are inoculated into a cultivation vessel and the inoculated cells are allowed to grow into a sheet (or a sheet-shaped cell culture). The sheet-forming cultivation is typically accomplished by inoculating cells (capable of growing into a sheet) into a culture vessel and cultivating the inoculated cells for a prescribed period under a condition that they bind together to react with one another. The cell binding condition is not specifically restricted but is one which is commonly used for cell cultivation at 37° C. in a 5% $CO_2$ atmosphere. Any adequate condition suitable for cells to be inoculated will be selected by those who are skilled in the art. Some examples of sheet-forming cultivation are found in the following literature without specific restrictions: Patent Document 1, JP-A-2010-081829, JP-A-2010-226991, JP-A-2011-110368, JP-A-2011-172925, and WO 2014/185517.

The cell inoculation may be accomplished in any known way under any known conditions. An exemplary method of cell inoculation is by injecting into a vessel a suspension of cells dispersed in a sheet-forming medium. The injection of cell suspension may be facilitated by using a tool, such as pipette and dropper, suitable for injection.

Inoculation with cells is not specifically restricted in the density of cells. Cells may exist in a density adequate for cells to form a sheet-shaped cell culture without substantial proliferation. The term "a density adequate for cells to form a sheet-shaped cell culture without substantial proliferation" denotes a cell density adequate for cells to form a sheet-shaped cell culture when cells are cultivated in a non-proliferative culture solution which is substantially free of growth factor. This inoculation density is higher than that used in the technique that employs a culture solution containing a growth factor; it may be equal to or higher than that for cells to confluent. An unrestricted example of the cell density is equal to or higher than $1.0 \times 10^5$ cells/cm$^2$. The cell density has no upper limit; but it may be lower than $3.4 \times 10^6$ cells/cm$^2$ so long as it has no adverse effect on the formation of the cell culture and it does not induce cell differentiation.

The density adequate for cells to form a sheet-shaped cell culture without substantial proliferation may vary over a certain range as indicated below depending on the embodiment: $1.0 \times 10^5$ to $3.4 \times 10^6$ cells/cm$^2$; $3.0 \times 10^5$ to $3.4 \times 10^6$ cells/cm$^2$; $3.5 \times 10^5$ to $3.4 \times 10^6$ cells/cm$^2$; $1.0 \times 10^6$ to $3.4 \times 10^6$ cells/cm$^2$; $3.0 \times 10^5$ to $1.7 \times 10^6$ cells/cm$^2$; $3.5 \times 10^5$ to $1.7 \times 10^6$ cells/cm$^2$; and $1.0 \times 10^6$ to $1.7 \times 10^6$ cells/cm$^2$. The above-mentioned ranges may include one of or both the upper limit and the lower limit, so long as the upper limit is less than $3.4 \times 10^6$ cells/cm$^2$. Examples of the above-mentioned density are as follows: equal to or higher than $3.0 \times 10^5$ cells/cm$^2$ and lower than $3.4 \times 10^6$ cells/cm$^2$ (including the lower limit and not including the upper limit); equal to or higher than $3.5 \times 10^5$ cells/cm$^2$ and lower than $3.4 \times 10^6$ cells/cm$^2$ (including the lower limit and not including the upper limit); equal to or higher than $1.0 \times 10^6$ cells/cm$^2$ and lower than $3.4 \times 10^6$ cells/cm$^2$ (including the lower limit and not including the upper limit); higher than $1.0 \times 10^6$ cells/cm$^2$ and lower than $3.4 \times 10^6$ cells/cm$^2$ (not including the lower limit and not including the upper limit); and higher than $1.0 \times 10^6$ cells/cm$^2$ and equal to or lower than $1.7 \times 10^6$ cells/cm$^2$ (not including the lower limit and including the upper limit).

The sheet forming is accomplished with the help of a medium, which is not specifically restricted so long as it has electrical conductivity. Examples of the medium include physiological saline, various physiological buffer solutions containing electrolytes (such as PBS and HBSS), and those which are derived from various basal media for cell cultivation. Examples of the basal media unrestrictedly include DMEM, MEM, F12, DME, RPMI1640, MCDB (such as MCDB 102, 104, 107, 120, 131, 153, and 199), L15, SkBM, RITC80-7, and DMEM/F12. These basal media are commercially available and have their composition known to public. The basal medium may be used in the form of its standard composition (or in the form as purchased); alternatively, it may be used in the form with its composition modified according to the cell species and cell condition. In other words, the basal medium to be used is not restricted to the one with known composition but includes the one which has one or more than one component added, deleted, or increased or decreased in amount. The medium for sheet formation may include such additives as serum (e.g., fetal bovine serum, bovine serum, horse serum, and human serum), and various growth factors (e.g., FGF, EGF, VEGF, and HGF).

Those cells which form the sheet-shaped cell culture unrestrictedly include adherent cells which are exemplified below. Somatic cells (such as cardiocytes, fibroblasts, epithelial cells, endothelial cells, hepatocytes, pancreatic cells, nephrocytes, adrenal cells, periodontal membrane cells, gingival cells, periosteal cells, dermal cells, synovial cells, and chondrocytes) and stem cells (such as myoblasts, tissue stem cells (e.g., cardiac stem cells), embryonic stem cells, pluripotent stem cells (e.g., iPS or induced pluripotent stem cells), and mesenchymal stem cells. The somatic cells may be those which have differentiated from stem cells, especially iPS cells. Also, those cells which form the sheet-shaped cell culture unrestrictedly include myoblasts (e.g., skeletal myoblasts), mesenchymal stem cells (e.g., those which are derived from marrow, fat tissues, peripheral blood, skin, hair root, muscle tissue, endometrium, placenta, and cord blood), cardiocytes, fibroblasts, heart stem cells, embryonic stem cells, iPS cells, synovial cells, chondrocytes, epithelial cells (e.g., oral mucosa epitheliocytes, retinal pigment epitheliocytes, and nasal mucosa epitheliocytes), endothelial cells (e.g., blood endothelial cells), hepatocytes (e.g., hepatic mesenchymal cells), pancreatic cells (e.g., islet cells), nephrocytes, adrenal cells, periodontal membrane cells, gingival cells, periosteal cells, and dermal cells).

The cell culture is examined for impedance and/or electrical resistance by any known technique. The impedance may be determined, for example, by applying an AC voltage and current to the cell culture and measuring an AC voltage and current that appear in the cell culture and dividing the voltage by the current. The electrical resistance may be determined, for example, by applying a DC voltage across the cell culture and measuring a current that flows across the cell culture (or applying a DC current across the cell culture and measuring a voltage that appears across the cell culture) and dividing the voltage by the current. The impedance and/or electrical resistance may be determined by using any known apparatus (such as impedance meter and resistance meter).

The voltage application may be accomplished in the following way, for example. The cell culture is allowed to grow between a working electrode and a counter electrode across which a current flows, and a voltage is applied across the two electrodes, with the cell culture placed between them. The voltage application may also be accomplished in another way that follows, for example. A working electrode and a counter electrode are arranged in the bottom of the cultivation vessel, on which the cell culture is allowed to grow, and a voltage is applied across the two electrodes. Alternatively, a voltage is applied across a working electrode and a counter electrode one of which is placed on the upper surface of the cell culture and the other of which is placed on the lower surface.

The impedance of the cell culture may be determined by any known method such as ECIS (Electric Cell-substrate Impedance Sensing) method. The electrical resistance of the cell culture may be determined by any known method such as ECIS method and TEER (Trans Epithelial Electric Resistance) measuring method. There are known and commercial apparatuses for determining the impedance and/or electrical resistance of the culture medium. (The former is disclosed in U.S. Pat. No. 5,187,096, and the latter is available as ECIS Z or ECIS Zθ from Applied BioPhysics, Inc. or as EVOM2 from World Precision Instruments, Inc.) These apparatuses may be used to evaluate the ability of cells to grow into a sheet.

In addition to the determination of the impedance and/or electrical resistance, the determination of impedance may be performed simultaneously with the determination of phase of voltage or current. The determination of phase of voltage or current may be performed by any known technique, such as the one which employs a lock-in amplifier. The thus determined phase of voltage or current may be used to determine the resistance and reactance from the impedance.

The AC current to be applied to determine impedance may have one or more than one frequency. The impedance varies depending on frequency because the cell culture existing between the two electrodes functions as a capacitor, as in the case of ECIS model mentioned later. Therefore, the difference in frequency can be used to evaluate the ability of cells to grow into a sheet. The frequency to be used is not specifically restricted so long as information on the ability of cells to grow into a sheet can be obtained. It may be selected from 31.25 Hz to 64 kHz and 4 to 64 kHz; particularly 62.5 Hz, 125 Hz, 250 Hz, 500 Hz, 1 kHz, 2 kHz, 4 kHz, 8 kHz, 16 kHz, 32 kHz, and 64 kHz.

The determination of impedance and/or electrical resistance of the cell culture may be performed periodically. The periodically repeated determinations permit one to detect and/or monitor the change with time of the impedance and/or electrical resistance. The interval of the periodical determinations is not specifically restricted; for example, it may be 0.001 seconds to 3 hours, 0.01 seconds to 1 hour, 0.05 seconds to 30 minutes, 0.1 seconds to 10 minutes, or 1 second to 1 minute. The determination of impedance and/or electrical resistance may be performed within a certain period of time which is long enough to provide information necessary to evaluate the ability of cells to grow into a sheet. Such a period may be within 72 hours, 48 hours, 36 hours, 24 hours, 12 hours, 10 hours, 8 hours, or 6 hours, for example.

The impedance and/or electrical resistance determined as mentioned above give numerical values relating thereto. Such numerical values may be determined as the impedance and/or electrical resistance is determined, or calculated from the impedance and/or electrical resistance, or calculated from the thus calculated numerical values. Those numerical values which are determined as the impedance is determined unrestrictedly include, for example, voltage, current, frequency of AC voltage, timing of determination (length of time from the start of sheet-forming cultivation), and the phase of voltage or current to be determined. Those numerical values which are determined as the electrical resistance is determined unrestrictedly include, for example, voltage, current, and timing of determination. Those numerical values which are calculated from the numerical values which are determined as the impedance is determined unrestrictedly include, for example, the electrical resistance of the cell culture, capacitance, Rb, $\alpha$, Cm, Rb/$\alpha$, peak values thereof, time to peak, slope to peak, coefficient of differential with respect to time, and change with time in amount or ratio within a prescribed period of time.

The ECIS model (see Giaever and Keese, Proc Natl Acad Sci USA, 1991 Sep. 1; 88(17): 7896-900, for example) tells that the impedance (Z) to be determined consists of resistance (R) and reactance (Xc) and the resistance is a quotient obtained by dividing voltage (in phase with current) by current, and the reactance is a quotient obtained by dividing voltage (out of phase with current) by current. The capacitance (C) is calculated from $Xc=1/(2\pi fC)$ and $Z=(R^2+Xc^2)^{0.5}$, where f represents frequency. Consequently, the impedance, current, voltage, phase, and frequency, which have been determined in the presence of the cell culture, permit one to calculate the electrical resistance and capacitance of the cell culture.

The ECIS model is also useful to calculate Rb, $\alpha$, and Cm. According to the ECIS model, the cells inoculated on the working electrode is regarded as a cylindrical body surrounded by an insulating film and filled with a conducive electrolyte. When the cylindrical body is given an AC current from the working electrode at the bottom thereof, the space between the cells functions as a resistance and the cells function as a capacitor as the current flows to the counter electrode. The ECIS model uses Rb to denote the resistance of the space between cells and also uses Cm to denote the capacitance of the cell membrane. The fact that the bottom of the cylindrical body is not in uniform contact with the electrode but in partial contact with the electrode leads to an assumption that there is a uniform gap (with a height of h) between the bottom and the electrode, and this assumption suggests the existence of a resistance across the bottom and the electrode. The ECIS model uses a to denote the resistance across the bottom and the electrode. Incidentally, $\alpha$ is defined as $\alpha=rc(\rho/h)^{0.5}$, where rc denotes the radius of the cell and $\rho$ denotes the resistance of the medium (in which cells grow into the sheet-shaped culture). The values of Rb and $\alpha$ can be calculated from the following formulas. (See Giaever and Keese, Opp et al., Biosens Bioelectron. 2009 Apr. 15; 24(8): 2625-9, for example.)

[Formula 1]

$$\frac{1}{Z_c} = \frac{1}{Z_n}\left[\frac{Z_n}{Z_n+Z_m} + \frac{\frac{Z_m}{Z_n+Z_m}}{\frac{\gamma r_c}{2}\frac{I_0(\gamma r_c)}{I_1(\gamma r_c)} + R_b\left(\frac{1}{Z_n}+\frac{1}{Z_m}\right)}\right] \quad (I)$$

$$\gamma r_c = r_c\sqrt{\frac{\rho}{h}\left(\frac{1}{Z_n}+\frac{1}{Z_m}\right)} = \alpha\sqrt{\left(\frac{1}{Z_n}+\frac{1}{Z_m}\right)} \quad (II)$$

$$Z_n = S\left(R_n + \frac{1}{i2\pi fC_n}\right) \quad (III)$$

$$Z_m = 2\left(\frac{1}{R_m} + i2\pi fC_m\right)^{-1} \quad (IV)$$

In the formula above, Zc denotes the impedance per unit area of the electrode (working electrode) covered with cells; Zn denotes the impedance per unit area of the electrode not covered with cells; Zm denotes the impedance per unit area of the cell culture; $I_0$ and $I_1$ denote respectively the zeroth and first order modified Bessel function of the first kind; S denotes the area of the electrode, Rn denotes the determined value of the resistance of the electrode not covered with cells; f denotes the frequency of the AC voltage; Cn denotes the determined value of the capacitance of the electrode not covered with cells; Rm denotes the resistance of the cell membrane; and Cm denotes the capacitance of the cell membrane. Incidentally, the parameters represented by R, C, Rb, $\alpha$, and Cm are available in the form of output from the software attached to ECISZ$\theta$ (Applied BioPhysics, Inc.). Rb/$\alpha$ is a quotient obtained by dividing Rb by $\alpha$.

The peak value and the time to peak denote respectively the numerical values of R, C, Rb, $\alpha$, Cm, and Rb/$\alpha$ at the time of their peak and the time to reach their peak. The slope to peak denotes a quotient obtained by dividing the peak value by the time to peak. As demonstrated in Example 3, it was found that, after inoculation with cells, R, Rb, $\alpha$, and Rb/$\alpha$ reach their peaks in a comparatively early stage of the period for sheet-forming cultivation and then they gradually decrease. This suggests that the numerical values relating to the peak can be used to judge in an early stage the ability of cells to grow into a sheet.

Step 2 in the method employs the reference values which are established to judge the degree of the ability of cells to grow into a sheet. The reference values can be established by preliminary experiments with cells for which the degree of the ability of cells to grow into a sheet is known. The degree of the ability of cells to grow into a sheet may be expressed in terms of two levels or three levels. The two levels consist of the "adequate" level representing the ability of cells to grow into a normal sheet and the "inadequate" level representing the lack of the ability of cells to grow into a normal sheet. The three levels consist of the "adequate" level representing the ability of cells to grow into a normal sheet, the "low" level representing the ability of cells to merely grow into a sheet (which is too weak to keep its shape when it is detached from the cultivation substrate), and the "excessive" level representing the ability of cells to merely grow into a sheet (which spontaneously detaches from the cultivation substrate before the period of sheet-forming cultivation comes to an end). There are certain reference values for judgment about which of the foregoing two levels or three levels the ability of cells to grow into a sheet corresponds to. Such reference values are not specifically restricted. For example, one reference value may specify the ratio of cells capable of growing into a sheet of a certain level. Another reference value may specify the ratio of cells capable of growing into a sheet of a certain level and the ratio of cells capable of growing into a sheet of another level. Such ratios may be 60%, 70%, 80%, 85%, 90%, 95%, 97%, 98%, 99%, and 100%. The higher ratio implies the higher reliability of the reference value.

The foregoing is exemplified in Table 13 for Example 3. Assume that the reference value for the peak value of electrical resistance is "smaller than 550Ω." Then, 100% of the cells having "low" ability to grow into a sheet satisfies this reference value, and none of the cells having the "adequate" and "excessive" ability to grow into a sheet satisfy this reference value. This implies that the foregoing reference value is extremely reliable for discrimination between those cells having the "low" ability to grow into a sheet and those cells having the "adequate" and "excessive" ability to grow into a sheet. Also, assume that the reference value for the time to peak of electrical resistance is "longer than 6 hours." Then, only 18% of those cells having the "low" ability to grow into a sheet satisfies this reference value, none of those cells having the "adequate" and "excessive" ability to grow into a sheet satisfy this reference value. This implies that those cells that satisfy this reference value almost apparently have the "low" ability to grow into a sheet. It is concluded, therefore, that the foregoing reference value is extremely reliable to judge that the cells have a "low" ability to grow into a sheet.

The reference value may be established for values of any kind or for values of specific kinds useful to evaluate the ability of cells to grow into a sheet. The kind of numerical values to evaluate the ability of cells to grow into a sheet is not specifically restricted. Appropriate numerical values for this purpose may be selected from those values representing the statistically significant difference among the groups of cells differing in the ability of cells to grow into a sheet. This will be explained below with reference to Tables 7 to 10 of Example 3. The numerical values for certain kinds indicated a statistically significant difference among those cells having the ability to grow into a weak sheet, those cells having the ability to grow into a normal sheet, and those cells merely having the ability to grow into a detached sheet. (For example, a statistically significant difference was found between weak sheet and normal sheet in R, Rb, peak value of Rb/α, slope to peak, and peak value of a. A statistically significant difference was also found between weak sheet and detached sheet in R, peak value of Rb, and slope to peak.) The foregoing suggests that the reference values established for numerical values of specific kinds lead to highly reliable reference values, as demonstrated in Tables 13 and 14.

The cell cultures vary in impedance and electrical resistance from one species of cells to another. This leads to an assumption that the reference values also vary depending on the species of cells and the ratio of the species of cells constituting the cell cultures. Fortunately, however, it would be possible for those who are skilled in the art to establish adequate reference values for the specific species of cells or for the cell population composed of cells in a specific ratio if they refer to this specification, particularly Examples given later herein. Thus, the specific reference values given herein are merely exemplary and are not intended to restrict the scope of the present invention.

The value determined in Step (1) is compared with the reference value in the following way. In the case where the reference value is a single value, comparison is achieved simply by determining whether the value determined in Step (1) is larger than, smaller than, equal to, equal to or larger than, or equal to or smaller than the reference value. In the case where the reference value has a certain range, comparison is achieved by determining whether the value determined in Step (1) is contained in the reference value range, larger than the upper limit, smaller than the lower limit, equal to or larger than the upper limit, or equal to or smaller than the lower limit.

The judgment in Step (3) as to the ability of cells to grow into a sheet is performed by comparing the numerical values obtained in Step (1) with the reference values. Such comparison reveals a correspondence between the numerical value and the level of ability, the correspondence depending on the properties of the reference value. For example, in the case where the reference value is a single value and there is a correspondence between the numerical value and the reference value such that any sample having a numerical value smaller than the reference value is regarded as cells having an "inadequate" ability to grow into a sheet and any sample having a numerical value equal to or larger than the reference value is regarded as cells having an "adequate" ability to grow into a sheet, a judgment is made to the effect that the sample has an "inadequate" ability to grow into a sheet if the numerical value determined in Step (1) is smaller than the reference value and the sample has an "adequate" ability to grow into a sheet if the numerical value determined in Step (1) is equal to or larger than the reference value. Also in the case where the reference value is expressed in terms of range and there is a correspondence between the numerical value and the range of the reference value such that any sample having a numerical value within the range of the reference value is regarded as cells having a "adequate" ability to grow into a sheet, any sample having a numerical value smaller than the lower limit of the range of the reference value is regarded as cells having a "low" ability to grow into a sheet, and any sample having a numerical value larger than the upper limit of the range of the reference value is regarded as cells having an "excessive" ability to grow into a sheet, a judgment is made to the effect that the sample has an "adequate" ability to grow into a sheet if the numerical value determined in Step (1) is within the range of the reference value, the sample has a "low" ability to grow into a sheet if the numerical value determined in Step (1) is smaller than the lower limit of the range of the reference value, and the sample has an "excessive" ability to grow into a sheet if the numerical value determined in Step (1) is larger than the upper limit of the range of the reference value.

Steps (2) and (3) may be performed once or more than once. For example, in the case where the ability of cells to grow into a sheet is to be determined in three or more levels, Steps (2) and (3) are performed repeatedly so that the ability of cells to grow into a sheet is determined level by level each time the Steps (2) and (3) are performed. This will be explained below in a concrete manner with reference to Example 3. In the case where the reference value for the peak of electrical resistance is set at "smaller than 550Ω," a discrimination may be made between those cells having a "low" ability to grow into a sheet and those cells having an "adequate" or "excessive" ability to grow into a sheet, but no satisfactory discrimination may be made between those cells having an "adequate" ability to grow into a sheet and those cells having an "excessive" ability to grow into a sheet. On the other hand, in the case where the reference value for the peak of Rb/α is set at "larger than 0.55 cm·Ω$^{0.5}$," a discrimination may be made between those cells having an "excessive" ability to grow into a sheet and those cells having a "low" or "adequate" ability to grow into a sheet, but no satisfactory discrimination may be made between those cells having a "low" ability to grow into a sheet and those cells having an "adequate" ability to grow into a sheet. This situation will be circumvented in the following way. Steps (2) and (3) are performed first to compare the numerical value determined in Step (1) with the reference value "smaller than 550Ω" for the peak of electrical resistance, thereby discriminating between those cells having a "low" ability to grow into a sheet and those cells having an "adequate" and "excessive" ability to grow into a sheet. Then, Steps (2) and (3) are performed for the second time to compare the numerical value determined in Step (1) with the reference value "larger than 0.55 cm·Ω$^{0.5}$" for the peak of Rb/α, thereby discriminating between those cells having an "adequate" ability to grow into a sheet and those cells having an "excessive" ability to grow into a sheet. All levels of the ability to grow into a sheet can thus be judged.

Figure 4:
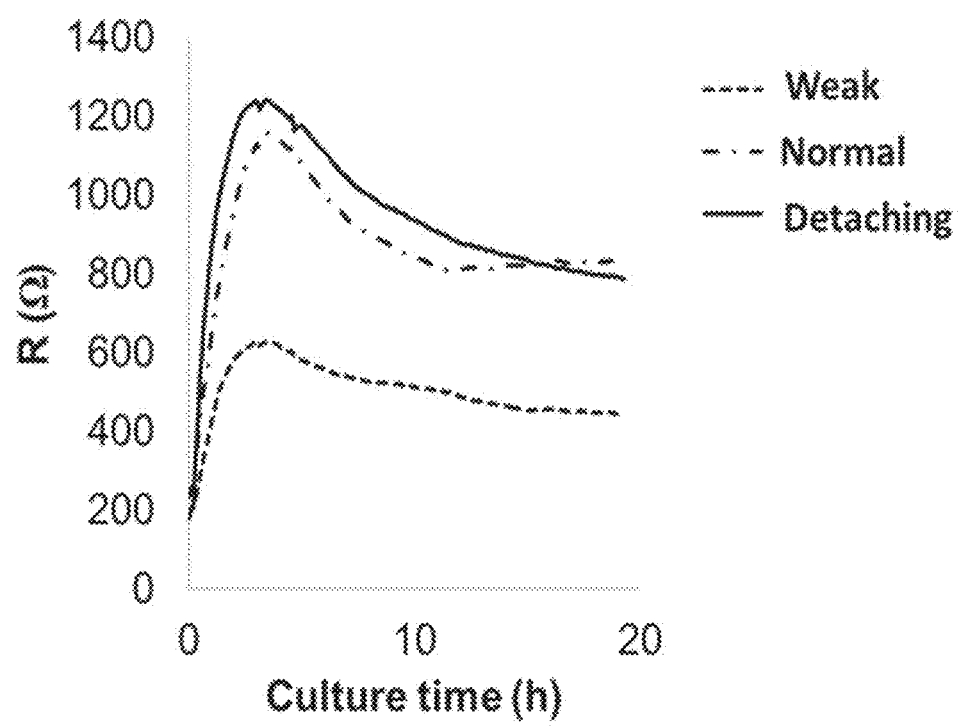
FIG. 4 is a graph depicting the change with time of electrical resistance (R) that takes place in a weak sheet, normal sheet, and detached sheet.
Figure 5:
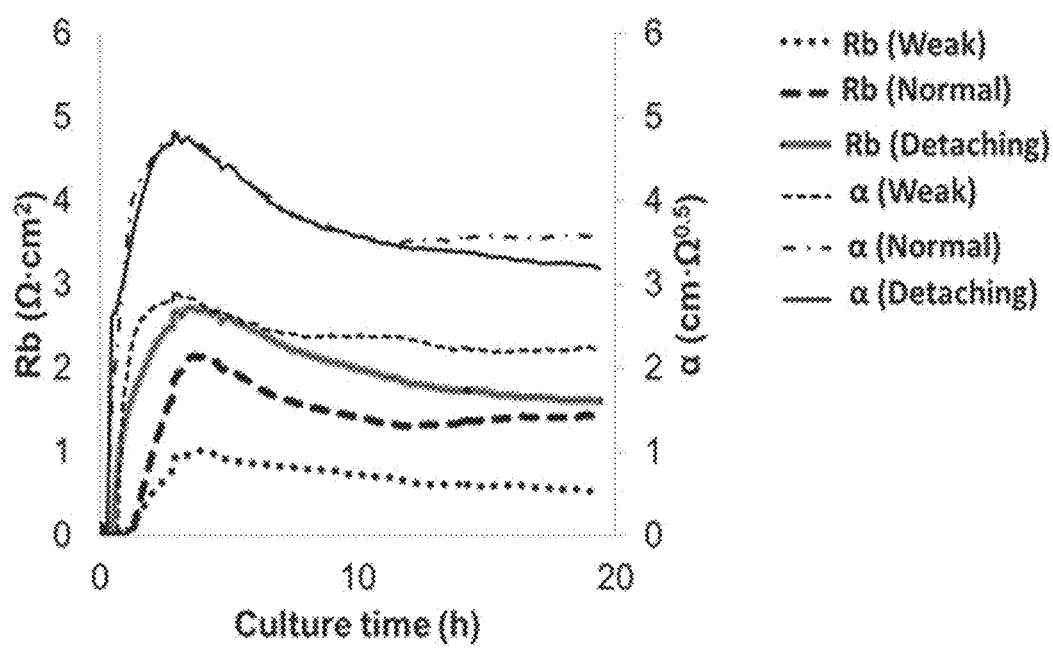
FIG. 5 is a graph depicting the change with time of Rb and a that takes place in a weak sheet, normal sheet, and detached sheet.

In Step (3) that is performed in one way, a judgment is made to the effect that cells have a low ability to grow into a sheet if the electrical resistance determined is equal to or smaller than the reference value. In Step (3) that is performed in another way, a judgment is made to the effect that cells have a low ability to grow into a sheet if Rb, α, and Rb/α are equal to or smaller than the reference value. In Step (3) that is performed in further another way, a judgment is made to the effect that cells have an adequate or excessive ability to grow into a sheet if Rb, α, and Rb/α are equal to or larger than the reference value. As depicted in FIGS. 4 and 5, the electrical resistance, Rb, α, and Rb/α are smaller in cells having a low ability to grow into a sheet than in cells having an adequate or excessive ability to grow into a sheet throughout the entire period of sheet-forming cultivation. Regardless of the way in which Step (3) is performed, the electrical resistance, Rb, α, and Rb/α may be measured at any time during the sheet-forming cultivation.

In Step (3) that is performed in another way, a judgment is made to the effect that cells have a low ability to grow into a sheet if the numerical value selected from the group consisting of the peak value of electrical resistance, the peak value of Rb, and the slope to the peak of Rb is equal to or smaller than the reference value, and/or if the numerical value selected from the group consisting of the time to peak of electrical resistance and the time to peak of Rb is equal to or larger than the reference value. In Step (3) that is performed in another way, a judgment is made to the effect that cells have an adequate ability to grow into a sheet if the numerical value selected from the group consisting of the time to peak of electrical resistance and the time to peak of Rb is equal to or smaller than the reference value and the numerical value selected from the group consisting of the peak value of Rb/α and the slope to the peak of Rb/α is equal to or smaller than the reference value, and/or if the numerical value selected from the group consisting of the time to the peak of electrical resistance and the time to the peak of Rb is equal to or smaller than the reference value and the time to the peak of Rb/α is equal to or longer than the reference value. In Step (3) that is performed in another way, a judgment is made to the effect that cells have an excessive ability to grow into a sheet if the numerical value selected from the group consisting of the peak value of Rb/α and the slope to the peak of Rb/α is equal to or larger than the reference value, and/or if the time to the peak of Rb/α is equal to or shorter than the reference value.

The present disclosure provides a method for evaluating the ability of cells to grow into a sheet as mentioned above. This method may be applied to a sheet-shaped cell culture to be practically used for transplantation, or to a sheet-shaped cell culture which represents a lot of sheet-shaped cell cultures produced under the same condition. In the latter case, this method gives a result of evaluation which can be applied to the entire lot to which the particular cell culture belongs. In this case, the result of evaluation may be used to control the production process for the entire lot to which the particular cell culture belongs. For example, if the result of evaluation suggests that the cells in question are low in ability to grow into a sheet, a remedy may be adopted to cope with such a situation. The remedy may be one which enhances the bond strength between cells, such as the addition of extracellular substrate components to the culture medium, the addition of factors that promote the production of extracellular substrate components to the culture medium, the use of a culture substrate coated with serum or extracellular substrate components, and the inoculation with a higher cell density. The extracellular substrate components include, for example, collagen, laminin, fibronectin, vitronectin, gelatin, proteoglycan, and glycosaminoglycan. The factors that promote the production of extracellular substrate components include, for example, ascorbic acid, derivatives thereof such as ascorbic acid diphosphate and ascorbic acid monophosphate, and salts thereof such as sodium salt and magnesium salt. Also, if the result of evaluation suggests that the cells in question have an excessive ability to grow into a sheet, a remedy may be adopted to cope with such a situation. The remedy may be one which enhances the bond between the culture substrate and the cells being cultivated. This object may be achieved by employing a culture substrate highly capable of adhesion to the cells being cultivated. Such a substrate may be CellBIND (registered trademark) (from Corning (registered trademark)), which has its surface negatively charged, and one which has its surface coated with an adhesion factor. Another remedy may be one which enhances the bond between the culture substrate and the cells being cultivated by coating the surface of the culture substrate with serum, extracellular substrate components, adhesion factors, etc. Another remedy may be accomplished by reduction of the time of cultivation for cells to grow into a sheet and frequent monitoring for the early detection of detaching of the sheet-shaped cell culture from the cultivating substrate. Such monitoring helps detect the sign of detaching in an early stage of cultivation.

Another aspect of the present disclosure relates to a method for producing a sheet-shaped cell culture which includes:

(1) a step of examining cell cultures growing into a sheet to determine their impedance and/or electrical resistance or numerical values relating thereto;

(2) a step of comparing the numerical values determined by Step (1) with reference values;

(3) a step of judging, based on the results of comparison obtained in Step (2), the ability of cells to grow into a sheet; and (4) a step of controlling, based on the result of judgment obtained in Step (3), the process of producing the sheet-shaped cell culture. The foregoing method may occasionally be abbreviated as "production method" or "controlled production method" hereinafter.

The controlled production method according to the present disclosure includes Steps (1) to (3), which define the method for evaluation of cells to grow into a sheet, as mentioned above.

Step (4) is intended to variously control, based on the results of judgment obtained in Step (3), the process for production of the sheet-shaped cell culture. The control of the production process may be applied to the sheet-shaped cell culture which is under sheet-forming cultivation according to Step (1) or the different sheet-shaped cell culture of cells belonging to the same cell lot. In the latter case, the different sheet-shaped cell culture may be produced while Steps (1) to (3) are going or after Steps (1) to (3) have finished. The method for production of the sheet-shaped cell culture is known; it is for example disclosed in Patent Document 1, JP-A-2010-081829, JP-A-2010-226991, JP-A-2011-110368, JP-A-2011-172925, and WO 2014/185517. If the results of Step (3) suggests that the cells in question are low in ability to grow into a sheet, a remedy may be adopted to cope with such a situation. The remedy may be one which enhances the bond strength between cells, such as the addition of extracellular substrate components to the culture medium, the addition of factors that promote the production of extracellular substrate components to the culture medium, the use of a culture substrate coated with serum or extracellular substrate components, and the inoculation with a higher cell density. The extracellular substrate components include, for example, collagen, laminin, fibronectin, vitronectin, gelatin, proteoglycan, and glycosaminoglycan. The factors that promote the production of extracellular substrate components include, for example, ascorbic acid, derivatives thereof such as ascorbic acid diphosphate and ascorbic acid monophosphate, and salts thereof such as sodium salt and magnesium salt. Also, if the result of Step (3) suggests that the cells in question have an excessive ability to grow into a sheet, a remedy may be adopted to cope with such a situation. The remedy may be one which enhances the bond between the culture substrate and the cells being cultivated. This object may be achieved by employing a culture substrate highly capable of adhesion to the cells being cultivated. Such a substrate may be CellBIND (registered trademark) (from Corning (registered trademark)), which has its surface negatively charged, and one which has its surface coated with an adhesion factor. Another remedy may be one which enhances the bond between the culture substrate and the cells being cultivated by coating the surface of the culture substrate with serum, extracellular substrate components, adhesion factors, etc. Another remedy may be accomplished by reduction of the time of cultivation for cells to grow into a sheet and frequent monitoring for the early detection of detaching of the sheet-shaped cell culture from the cultivating substrate. Such monitoring helps detect the sign of detaching in an early stage of cultivation.

Another aspect of the present disclosure relates to a system for evaluating the ability of cells to grow into a sheet, the system having a container for cultivation in which cells are grown into a sheet and an apparatus for measuring the impedance and/or electrical resistance of the cell culture in the container. This system will occasionally be abbreviated as "sheet-forming ability evaluation system" hereinafter. This system will be employed for the method for evaluation of sheet-forming ability or the production method, which are defined in the present disclosure.

The sheet-forming ability evaluation system according to the present disclosure employs a container for cell cultivation, which is not specifically restricted so long as it is suitable for cultivation of cells that grow into a sheet. Such a container may be any conventional known one for cell cultivation. The container for cell cultivation should preferably be one which is made of any material impervious to the cultivation medium and is so constructed as to prevent the permeation of the cultivation medium. Such a material may be exemplified by polyethylene, polypropylene, Teflon (registered trademark), polyethylene terephthalate, polymethyl methacrylate, nylon-6,6, polyvinyl alcohol, cellulose, silicone, polystyrene, glass, polyacrylamide, and polydimethylacrylamide.

The container for cell cultivation may be provided with a working electrode and/or a counter electrode for determination of impedance and/or electrical resistance. The working electrode and/or the counter electrode may be arranged in any manner so long as they provide information necessary for determination of the impedance and/or electrical resistance of the cell culture. It is possible to arrange both the working electrode and the counter electrode on the inside of the bottom of the container for cultivation. It is also possible to arrange either of the working electrode and the counter electrode on that bottom of the container with which the base of the cell culture comes into contact and to arrange the other of the working electrode and the counter electrode above the upper side of the cell culture. The electrodes may be formed from any material without specific restrictions so long as it permits application of voltage to the cell culture and the cultivation medium for cells to grow into a sheet. Examples of such a material include gold, silver, platinum, carbon, indium-tin oxide, and the like. Cells may be inoculated on the electrodes or within an insert which is placed in the container, the insert being capable of permeating the medium for cultivation of cells to grow into a sheet. Particular examples of the container for cell cultivation include arrays (8W1E, 8W10E, 8W10E+, 8W1F, 8W1E DD, 8W2× 1E (from Applied BioPhysics, Inc.)) for commercially available ECIS (from Applied BioPhysics, Inc.).

No specific restrictions are imposed on the measuring apparatus for the sheet-forming ability evaluation system defined in the present disclosure, so long as it is capable of determining the impedance and/or electrical resistance of the cell culture. Any known impedance measuring apparatus and resistance meter may be used. These apparatus and meter may be constructed such that they are electrically connected to the electrodes in the case where the container for cultivation is provided with the electrodes. In the case where the container for cultivation is not provided with electrodes, the measuring apparatus may be connected to the container for cultivation in which the electrodes are arranged. The measuring apparatus should preferably be one which is capable of determining impedance and/or electrical resistance periodically. The interval of measurement is not specifically restricted and may be 0.001 seconds to 3 hours, 0.01 seconds to 1 hour, 0.05 seconds to 30 minutes, 0.1 seconds to 10 minutes, 1 second to 1 minute, or the like. The length of time for determination of impedance and/or electrical resistance is not specifically restricted, so long as it is sufficient to collect information for evaluation of the ability of cells to grow into a sheet; for example within 72 hours, 48 hours, 36 hours, 24 hours, 12 hours, 10 hours, 8 hours, or 6 hours.

The measuring apparatus may also be one which is further capable of determining the phase of voltage or current. It is possible to determine the phase of voltage or current by any known method that, for example, employs a lock-in amplifier. In other words, the measuring apparatus may be one which is provided with means, such as lock-in amplifier, which determines the phase of voltage or current.

The measuring apparatus may be one which is capable of determining the impedance at one frequency or more than one frequency. The frequency to which the measuring apparatus is applied is not specifically restricted so long it is capable of collecting information about the ability of cells to grow into a sheet. Examples of such frequencies are 31.25 Hz to 64 kHz and 4 to 64 kHz, preferably 62.5 Hz, 125 Hz, 250 Hz, 500 Hz, 1 kHz, 2 kHz, 4 kHz, 8 kHz, 16 kHz, 32 kHz, and 64 kHz.

The sheet-forming ability evaluation system according to the present system may have any construction suitable for evaluation of the ability of cells to grow into a sheet. Such a construction may include a processor to record and process the data of impedance and/or electrical resistance supplied from the measuring apparatus, an interface such as display unit and input unit, an injector to add cells and cultivation media to the container, an incubator for cell cultivation, and a stirrer.

The system for evaluating the ability of cells to grow into a sheet according to the present disclosure may be communicatably connected to or built into the system for producing the sheet-shaped cell cultures, so that it controls the process of production of the sheet-shaped cell cultures. Consequently, the present disclosure relates also to a system for producing the sheet-shaped cell cultures, the system having communicatably connected thereto the system for evaluating the ability of cells to grow into a sheet according to the present disclosure or having built therein the system for evaluating the ability of cells to grow into a sheet according to the present invention. The process for production of the sheet-shaped cell cultures is controlled in accordance with the evaluation of the ability of cells to grow into a sheet as mentioned above in relation to the production method according to the present disclosure.

EXAMPLES

The following Examples are illustrative and not intended to restrict the scope of the invention.

Example 1

Classification of Cells According to the Ability to Grow into a Sheet

Figure 2:
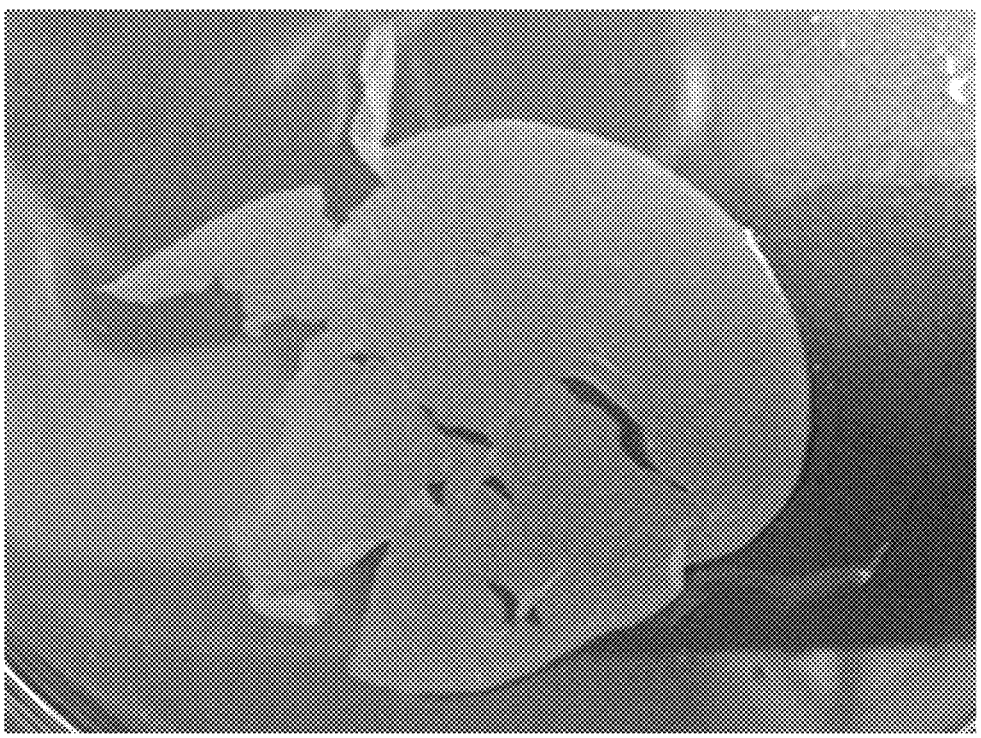
FIG. 2 is a photograph depicting the appearance of a weak sheet.
Figure 3:
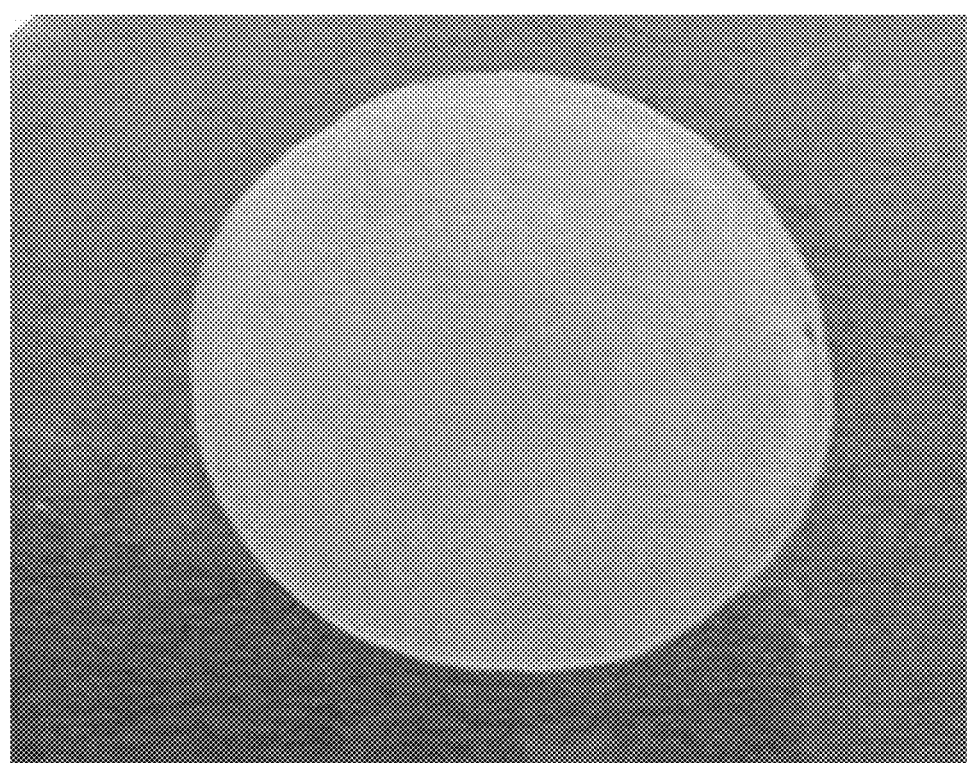
FIG. 3 is a photograph depicting the appearance of a normal sheet.

Blastocytes of skeletal muscle were prepared by usual way from different samples of human skeletal muscle. A portion of the blastocytes was suspended in a culture medium containing 20% human serum (DMEM-F12 from Life Technologies). The suspended cells were inoculated on a temperature-responsive culture dish (UpCell (registered trademark) with 12 wells, from CellSeed), with the number of cells being $3.7 \times 10^7$. Cultivation for the cells to grow into a sheet was carried out at 37° C. in a 5% $CO_2$ environment for 12 to 26 hours. After the cultivation, the resulting cell cultures were observed to check for their state. The resulting sheet-shaped cell cultures were divided into two classes; one which has detached from the culture dish (depicted in FIG. 1) and one which remains sticking to the culture dish. Those cells which have formed sheet-shaped cell cultures are classified as "detached sheet group." Those cell cultures which have remained sticking to the culture dish were detached by cooling the environment for cultivation down to room temperature. Some samples of the cell cultures broke (without keeping the sheet form) during the detaching step, whereas some samples of the cell cultures kept the sheet form (without breaking). The cells in the former case are designated as "weak sheet group" (depicted in FIG. 2), and the cells in the latter case are designated as "normal sheet group" (depicted in FIG. 3).

Example 2

Measurement of Electrical Characteristic Properties in the Course of Sheet-Forming Cultivation The "weak sheet," "normal sheet," and "detached sheet" which have been identified in Example 1 were examined to evaluate the state of cell adhesion. This object was achieved as follows by measuring the electrical characteristic properties of the cell sheet in the course of sheet-forming cell cultivation by using the real-time cell analyzing apparatus ECISZθ (from Applied BioPhysics, Inc.). ECISZθ is so designed as to measure in real time the impedance, voltage, and its phase of the cell layer on the electrodes. It also calculates several parameters, such as electrical resistance (R) and capacitance (C) of the cell layer, Rb as an index indicating the state of cells adhering to one another, a as an index indicating the state of adhesion between the cells and the electrodes (or the culture substrate), and Cm representing an average capacitance of the cell membrane. (Refer to Operation Manual for all ECIS Systems, Version 1.2.78, Applied BioPhysics, Inc.)

The cells of each group classified in Example 1 were inoculated on the well plate provided with electrodes (8W10E+, from Applied BioPhysics, Inc.) at a density of $8.57 \times 10^5$ cells/well. The inoculated cells underwent sheet-forming cultivation in DMEM-F12 culture medium containing 20% human serum at 37° C. in a 5% $CO_2$ environment. During the cultivation, the impedance, voltage, and its phase were measured and recorded time to time in MFT (Multiple Frequency/Time) mode with the help of ECISZθ. The measurement was carried out at frequencies of 62.5, 125, 250, 500, 1000, 2000, 4000, 8000, 16000, 32000, and 64000 Hz. The result of measurement at 8000 Hz was used in the experiment described below. The equipment for measurement was operated in accordance with the maker's manual. The thus measured values were converted into parameters with the help of software attached to the equipment.

Example 3

Identification of Indexes Relating to the Ability of Cells to Grow into a Sheet

Typical experiments with each group indicated that the electrical resistance (R) varies with time in the course of sheet-forming cultivation as depicted in FIG. 4. It is noted from FIG. 4 that the group of weak sheet has a smaller value of electrical resistance than other groups. This suggests that a smaller value of electrical resistance can be an index for the weak sheet. It is also noted that the electrical resistance rapidly increases in the early stage of sheet-forming cultivation and then gradually decreases after it has reached the peak.

Figure 6:
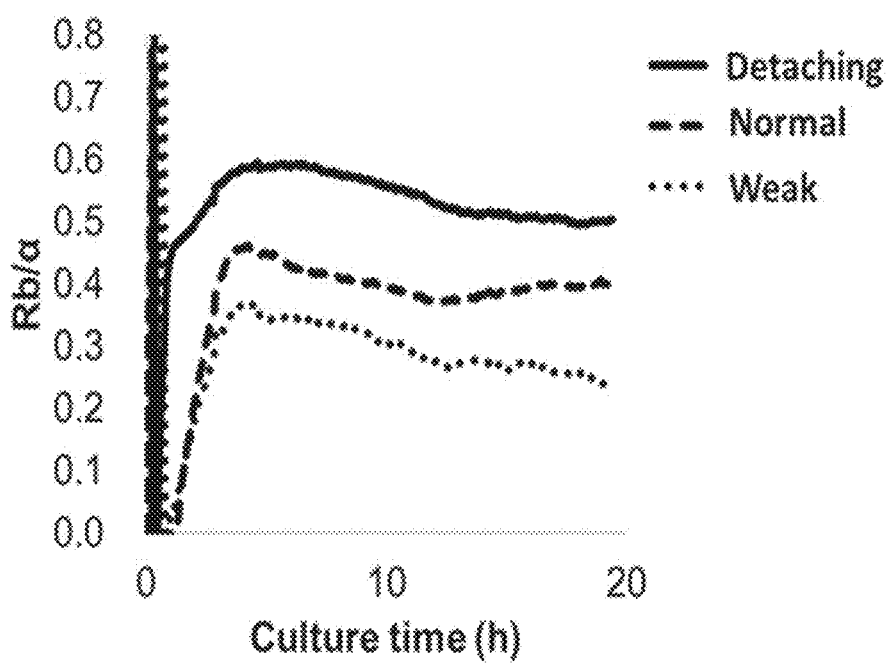
FIG. 6 is a graph depicting the change with time of Rb/α that takes place in a weak sheet, normal sheet, and detached sheet.

Typical experiments with each group indicate that Rb and α vary with time in the course of sheet-forming cultivation as depicted in FIG. 5. It is noted from FIG. 5 that the group of weak sheet has a smaller value of Rb than other groups. This suggests that a smaller value of Rb can be an index for the weak sheet. It also noted from FIG. 5 that the group of detached sheet has a value of α which is almost equal to that of the group of normal sheet but the group of detached sheet has a value of Rb which is larger than that of the group of normal sheet. This suggests that the group of detached sheet differs from the other group in that it has a relatively larger value of Rb than a value of α. This was made more apparent by graphical representation for Rb/α (Rb divided by α). It is considered that the value of Rb/α indicates the ease with which the cell culture detaches from the culture substrate (ability of cells to peel off). It is apparent from FIG. 6 that the group of detached sheet has a remarkably larger value of Rb/α than other groups.

Figure 7:
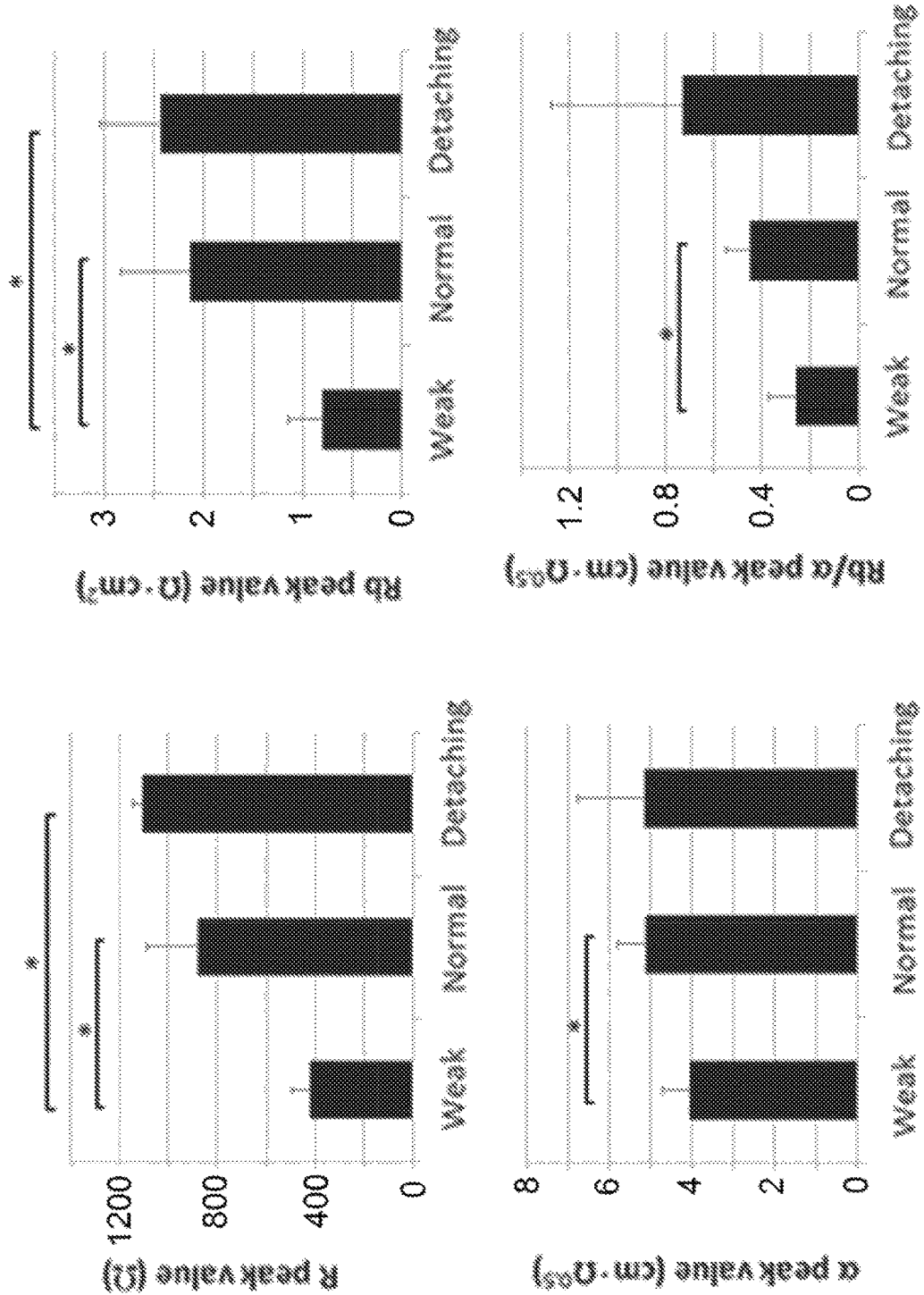
FIG. 7 is a graph depicting the peak values of electrical resistance (R), Rb, α, and Rb/α which are observed in a weak sheet, normal sheet, and detached sheet. The asterisk (*) denotes $p<0.005$.
Figure 8:
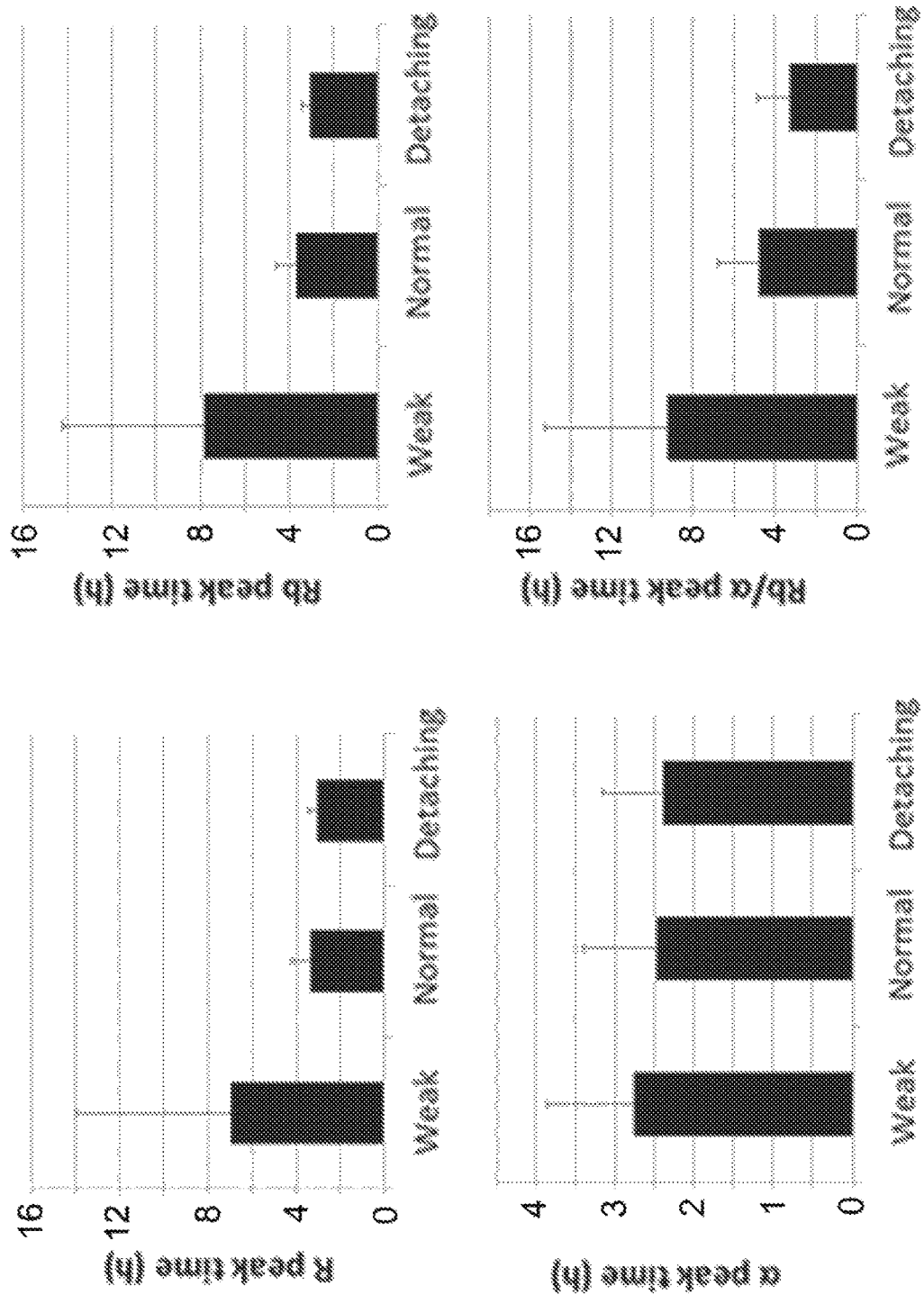
FIG. 8 is a graph depicting the time to peak of electrical resistance (R), Rb, α, and Rb/α which are observed in a weak sheet, normal sheet, and detached sheet.
Figure 9:
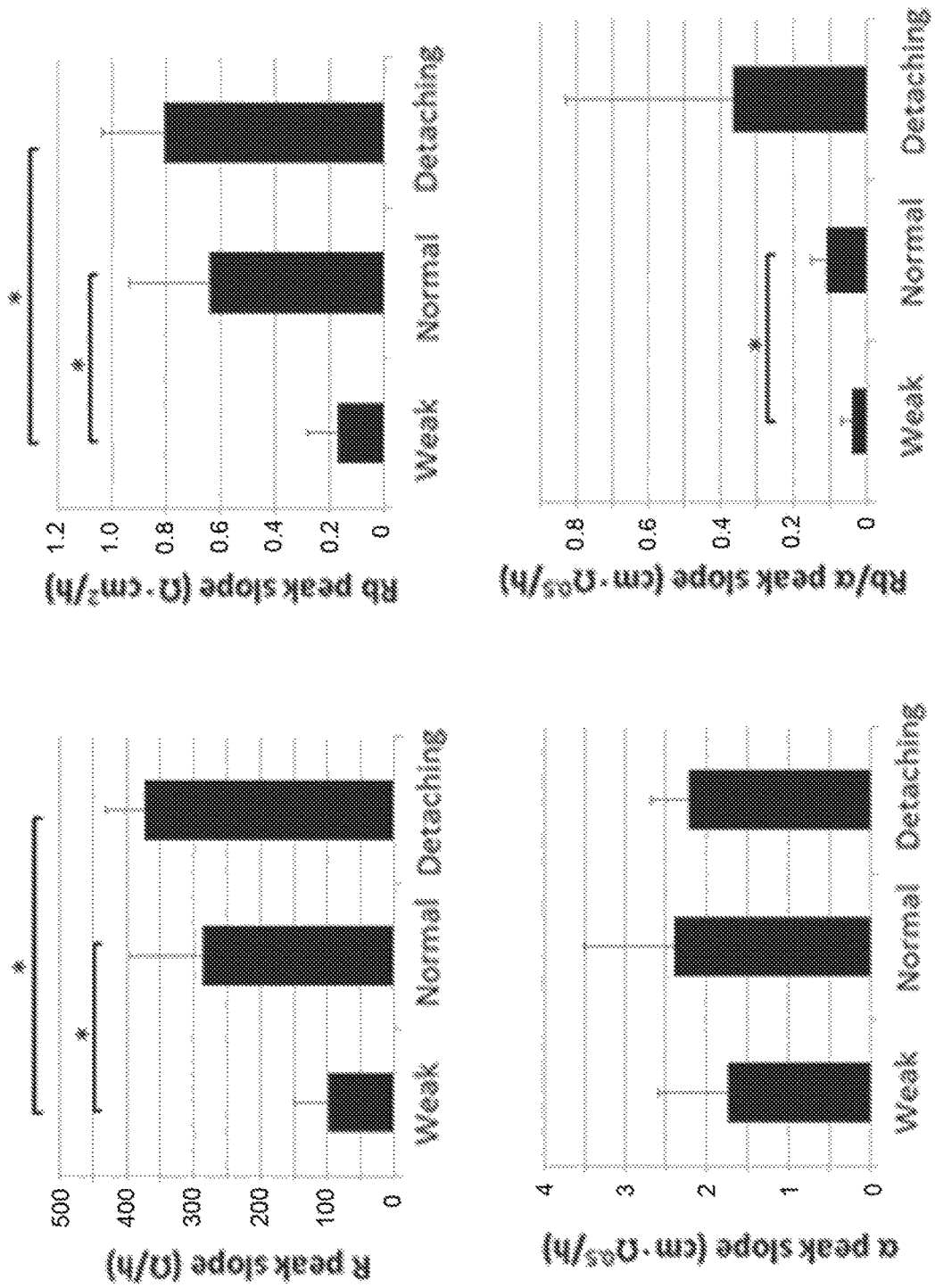
FIG. 9 is a graph depicting the slope to peak of electrical resistance (R), Rb, α, and Rb/α which are observed in a weak sheet, normal sheet, and detached sheet. The asterisk (*) denotes $p<0.005$.

Experiments were carried out to see if the index indicating the ability of cells to grow into a sheet can be obtained from such parameters as R, Rb, α, and Rb/α in terms of their peak values (the highest values that reach during sheet-forming cultivation), their time to peak (time for these values to take to reach the peak value), and their slope to peak (peak value divided by time to peak). The results of the experiments are indicated below in terms of the number of cells of each group and the average value of each group. The average value of each group is depicted in FIGS. 7 to 9.

TABLE 1

Numerical values for each group of weak sheet (Part 1)

| | R | | | Rb | | |
|---|---|---|---|---|---|---|
| No. | Peak value (Ω) | Time to peak (h) | Slope to peak (Ω/h) | Peak value (Ω · cm$^2$) | Time to peak (h) | Slope to peak (Ω · cm$^2$/h) |
| 1 | 501.5 | 20.6 | 24.4 | 1.22 | 6.53 | 0.19 |
| 2 | 442.1 | 3.0 | 146.6 | 1.02 | 3.72 | 0.27 |
| 3 | 403.6 | 3.4 | 120.1 | 0.91 | 4.13 | 0.22 |
| 4 | 542.1 | 3.8 | 143.4 | 1.31 | 3.78 | 0.35 |
| 5 | 508.2 | 2.6 | 179.0 | 1.01 | 3.62 | 0.28 |
| 6 | 361.9 | 4.6 | 79.3 | 0.53 | 6.52 | 0.08 |
| 7 | 327.7 | 2.7 | 119.4 | 0.47 | 20.52 | 0.02 |
| 8 | 338.9 | 21.6 | 15.7 | 0.40 | 20.66 | 0.02 |
| 9 | 339.1 | 4.8 | 70.0 | 0.26 | 6.46 | 0.04 |
| 10 | 399.2 | 5.3 | 75.9 | 0.66 | 5.47 | 0.12 |
| 11 | 437.8 | 4.0 | 109.4 | 0.96 | 4.28 | 0.22 |
| Average | 418.4 | 7.0 | 98.5 | 0.80 | 7.79 | 0.17 |
| SD | 74.7 | 7.0 | 50.9 | 0.35 | 6.43 | 0.11 |

TABLE 2

Numerical values for each group of weak sheet (Part 2)

| | α | | | Rb/α | | |
|---|---|---|---|---|---|---|
| No. | Peak value (cm · Ω$^{0.5}$) | Time to peak (h) | Slope to peak (cm · Ω$^{0.5}$/h) | Peak value (cm · Ω$^{0.5}$) | Time to peak (h) | Slope to peak (cm · Ω$^{0.5}$/h) |
| 1 | 3.29 | 3.51 | 0.94 | 0.42 | 8.15 | 0.052 |
| 2 | 2.92 | 2.89 | 1.01 | 0.37 | 4.57 | 0.081 |
| 3 | 4.07 | 1.66 | 2.45 | 0.31 | 11.70 | 0.027 |
| 4 | 4.06 | 1.24 | 3.27 | 0.35 | 4.90 | 0.072 |
| 5 | 3.65 | 1.46 | 2.47 | 0.34 | 4.48 | 0.070 |
| 6 | 3.63 | 3.48 | 1.04 | 0.23 | 7.37 | 0.032 |
| 7 | 3.78 | 2.33 | 1.62 | 0.21 | 20.73 | 0.010 |
| 8 | 4.27 | 3.93 | 1.09 | 0.11 | 20.78 | 0.005 |
| 9 | 4.76 | 4.21 | 1.13 | 0.07 | 7.08 | 0.009 |
| 10 | 4.86 | 8.86 | 1.26 | 0.17 | 6.18 | 0.028 |
| 11 | 5.06 | 1.77 | 2.56 | 0.25 | 5.19 | 0.047 |
| Average | 4.03 | 2.76 | 1.74 | 0.26 | 9.22 | 0.039 |
| SD | 0.67 | 1.10 | 0.86 | 0.11 | 6.04 | 0.027 |

TABLE 3

Numerical values for each group of normal sheet (Part 1)

| | R | | | Rb | | |
|---|---|---|---|---|---|---|
| No. | Peak value (Ω) | Time to peak (h) | Slope to peak (Ω/h) | Peak value (Ω · cm$^2$) | Time to peak (h) | Slope to peak (Ω · cm$^2$/h) |
| 1 | 922.2 | 3.5 | 262.8 | 2.15 | 3.65 | 0.59 |
| 2 | 1336.1 | 3.4 | 397.7 | 3.73 | 3.43 | 1.09 |
| 3 | 550.8 | 3.9 | 143.0 | 1.23 | 3.99 | 0.31 |
| 4 | 536.0 | 3.7 | 144.4 | 1.31 | 4.13 | 0.32 |
| 5 | 994.0 | 4.5 | 220.0 | 2.70 | 4.52 | 0.60 |
| 6 | 865.3 | 4.7 | 185.6 | 2.22 | 4.81 | 0.46 |
| 7 | 818.8 | 5.0 | 165.4 | 2.18 | 5.02 | 0.43 |
| 8 | 933.0 | 4.4 | 213.3 | 2.42 | 4.37 | 0.55 |
| 9 | 1039.5 | 2.6 | 396.1 | 2.60 | 2.77 | 0.94 |
| 10 | 872.2 | 2.6 | 341.6 | 1.41 | 3.83 | 0.37 |
| 11 | 1036.4 | 2.7 | 384.4 | 2.59 | 2.70 | 0.96 |
| 12 | 733.3 | 3.6 | 206.4 | 1.66 | 3.98 | 0.42 |
| 13 | 1002.4 | 2.5 | 406.6 | 2.42 | 2.74 | 0.88 |
| 14 | 959.7 | 2.4 | 400.6 | 2.33 | 2.6 | 0.90 |
| 15 | 715.6 | 2.5 | 282.3 | 1.50 | 3.16 | 0.47 |
| 16 | 468.8 | 3.2 | 145.0 | 0.75 | 5.26 | 0.14 |
| 17 | 967.6 | 2.5 | 381.7 | 2.49 | 2.54 | 0.98 |
| 18 | 1005.2 | 2.2 | 459.6 | 2.57 | 2.40 | 1.07 |
| Average | 875.4 | 3.3 | 285.3 | 2.13 | 3.66 | 0.64 |
| SD | 212.6 | 0.9 | 110.0 | 0.70 | 0.92 | 0.30 |

TABLE 4

Numerical values for each group of normal sheet (Part 2)

| | α | | | Rb/α | | |
|---|---|---|---|---|---|---|
| No. | Peak value (cm · Ω$^{0.5}$) | Time to peak (h) | Slope to peak (cm · Ω$^{0.5}$/h) | Peak value (cm · Ω$^{0.5}$) | Time to peak (h) | Slope to peak (cm · Ω$^{0.5}$/h) |
| 1 | 4.82 | 2.88 | 1.67 | 0.46 | 4.22 | 0.109 |
| 2 | 6.19 | 3.29 | 1.88 | 0.63 | 4.41 | 0.143 |
| 3 | 4.14 | 1.66 | 2.49 | 0.37 | 11.50 | 0.032 |
| 4 | 4.98 | 1.59 | 3.13 | 0.31 | 5.33 | 0.058 |
| 5 | 5.02 | 4.30 | 1.17 | 0.55 | 5.17 | 0.106 |
| 6 | 4.91 | 4.09 | 1.20 | 0.46 | 5.24 | 0.088 |
| 7 | 4.62 | 3.94 | 1.17 | 0.48 | 5.67 | 0.084 |

TABLE 4-continued

Numerical values for each group of normal sheet (Part 2)

| | α | | | Rb/α | | |
|---|---|---|---|---|---|---|
| No. | Peak value (cm · $\Omega^{0.5}$) | Time to peak (h) | Slope to peak (cm · $\Omega^{0.5}$/h) | Peak value (cm · $\Omega^{0.5}$) | Time to peak (h) | Slope to peak (cm · $\Omega^{0.5}$/h) |
| 8 | 4.98 | 3.04 | 1.64 | 0.50 | 5.53 | 0.090 |
| 9 | 5.09 | 2.34 | 2.18 | 0.52 | 3.20 | 0.163 |
| 10 | 5.81 | 1.70 | 3.42 | 0.29 | 4.84 | 0.059 |
| 11 | 5.18 | 2.27 | 2.28 | 0.52 | 3.27 | 0.159 |
| 12 | 4.50 | 1.48 | 3.04 | 0.39 | 3.98 | 0.097 |
| 13 | 4.89 | 2.40 | 2.04 | 0.53 | 4.07 | 0.130 |
| 14 | 4.83 | 2.19 | 2.21 | 0.50 | 2.95 | 0.169 |
| 15 | 5.05 | 1.77 | 2.85 | 0.37 | 3.65 | 0.100 |
| 16 | 4.58 | 2.19 | 2.09 | 0.28 | 7.02 | 0.040 |
| 17 | 5.14 | 1.98 | 2.60 | 0.51 | 3.09 | 0.165 |
| 18 | 7.21 | 1.21 | 5.96 | 0.43 | 3.09 | 0.138 |
| Average | 5.11 | 2.46 | 2.39 | 0.45 | 4.79 | 0.107 |
| SD | 0.69 | 0.93 | 1.11 | 0.10 | 2.01 | 0.043 |

TABLE 5

Numerical values for each group of detached sheet (Part 1)

| | R | | | Rb | | |
|---|---|---|---|---|---|---|
| No. | Peak value ($\Omega$) | Time to peak (h) | Slope to peak ($\Omega$/h) | Peak value ($\Omega \cdot cm^2$) | Time to peak (h) | Slope to peak ($\Omega \cdot cm^2$/h) |
| 1 | 1065.1 | 3.5 | 303.5 | 2.73 | 3.51 | 0.78 |
| 2 | 1093.0 | 2.6 | 416.4 | 2.83 | 2.70 | 1.05 |
| 3 | 1147.0 | 2.9 | 394.1 | 1.71 | 2.91 | 0.59 |
| Average | 1101.7 | 3.0 | 371.4 | 2.42 | 3.04 | 0.80 |
| SD | 41.6 | 0.5 | 59.8 | 0.62 | 0.42 | 0.23 |

TABLE 6

Numerical values for each group of detached sheet (Part 2)

| | α | | | Rb/α | | |
|---|---|---|---|---|---|---|
| No. | Peak value (cm · $\Omega^{0.5}$) | Time to peak (h) | Slope to peak (cm · $\Omega^{0.5}$/h) | Peak value (cm · $\Omega^{0.5}$) | Time to peak (h) | Slope to peak (cm · $\Omega^{0.5}$/h) |
| 1 | 4.80 | 2.88 | 1.67 | 0.59 | 4.64 | 0.128 |
| 2 | 3.65 | 1.48 | 2.47 | 1.33 | 4.48 | 0.899 |
| 3 | 6.39 | 2.77 | 2.50 | 0.25 | 3.62 | 0.070 |
| Average | 5.13 | 2.38 | 2.21 | 0.73 | 3.25 | 0.365 |
| SD | 1.66 | 0.78 | 0.47 | 0.55 | 1.61 | 0.463 |

The results of the foregoing experiments lead to the following conclusion.

(1) Those cells which grow into a weak sheet have parameters which all have small peak values, extremely small values particularly for R and Rb.

(2) Those cells which grow into a normal sheet or a detached sheet have parameters which all have large peak values. Those cells which grow into a detached sheet have a large peak value particularly of Rb/α.

(3) Those cells which grow into a weak sheet have parameters which all have a long time to peak, an extremely long time to peak particularly for R, Rb, and Rb/α.

(4) Those cells which grow into a normal sheet or a detached sheet have parameters which all have a short time to peak. Those cells which grow into a detached sheet have a short time to peak particularly for Rb/α.

(5) Those cells which grow into a weak sheet have parameters which all have a small slope to peak, extremely small slope to peak particularly for R, Rb, and Rb/α.

(6) Those cells which grow into a normal sheet or a detached sheet have parameters which all have a large slope to peak. Those cells which grow into a detached sheet have a large slope to peak particularly for Rb/α.

The foregoing numerical values were examined to see if there is any statistically significant difference among the groups. The results are indicated in FIGS. 7 to 10, in which "value," "time," and "slope" denote respectively "peak value," "time to peak," and "slope to peak."

TABLE 7

Results of statistical analysis of numerical values for each group (Part 1)

| | R | | | Rb | | |
|---|---|---|---|---|---|---|
| | Value ($\Omega$) | Time (h) | Slope ($\Omega$/h) | Value ($\Omega \cdot cm^2$) | Time (h) | Slope ($\Omega \cdot cm^2$/h) |
| Weak × Normal | 0.000 | 0.176 | 0.000 | 0.000 | 0.090 | 0.000 |
| Weak × Detached | 0.000 | 0.140 | 0.000 | 0.000 | 0.052 | 0.000 |
| Normal × Detached | 0.131 | 0.857 | 0.313 | 0.750 | 0.405 | 0.558 |

TABLE 8

Results of statistical analysis of numerical values for each group (Part 2)

| | α | | | Rb/α | | |
|---|---|---|---|---|---|---|
| | Value (cm · $\Omega^{0.5}$) | Time (h) | Slope (cm · $\Omega^{0.5}$/h) | Value (cm · $\Omega^{0.5}$) | Time (h) | Slope (cm · $\Omega^{0.5}$/h) |
| Weak × Normal | 0.001 | 0.667 | 0.164 | 0.000 | 0.056 | 0.000 |
| Weak × Detached | 0.559 | 0.882 | 0.580 | 0.417 | 0.187 | 0.520 |
| Normal × Detached | 1.479 | 0.558 | 1.458 | 0.714 | 1.187 | 0.654 |

TABLE 9

Results of statistical analysis of numerical values for each group (Part 3)

| | R | | | Rb | | |
|---|---|---|---|---|---|---|
| | Value ($\Omega$) | Time (h) | Slope ($\Omega$/h) | Value ($\Omega \cdot cm^2$) | Time (h) | Slope ($\Omega \cdot cm^2$/h) |
| Weak × Normal · Detached | 0.000 | 0.059 | 0.000 | 0.000 | 0.030 | 0.000 |
| Normal × Detached | 0.044 | 0.286 | 0.104 | 0.250 | 0.135 | 0.186 |

TABLE 10

Results of statistical analysis of numerical values for each group (Part 4)

| | α | | | Rb/α | | |
|---|---|---|---|---|---|---|
| | Value (cm · $Ω^{0.5}$) | Time (h) | Slope (cm · $Ω^{0.5}$/h) | Value (cm · $Ω^{0.5}$) | Time (h) | Slope (cm · $Ω^{0.5}$/h) |
| Weak × Normal · Detached | 0.000 | 0.222 | 0.055 | 0.000 | 0.019 | 0.000 |
| Normal × Detached | 0.493 | 0.186 | 0.486 | 0.238 | 0.396 | 0.218 |

Tables 7 and 8 indicate the results of the statistical analysis which was performed by t-test on the numerical values obtained from each of the group of weak sheet, the group of normal sheet, and the group of detached sheet. Tables 9 and 10 indicate the results of the statistical analysis performed by t-test on the numerical value obtained from the group of weak sheet and the numerical values obtained from the group of normal sheet and the group of detached sheet which are combined together (indicated by "Weak× Normal·Detached"). Tables 9 and 10 also indicate the results of the statistical analysis performed by t-test on the numerical values obtained from the group of normal sheet and the group of detached sheet which are combined together (indicated by "Normal×Detached"). The analysis by t-test was performed after the analysis by F-test. The t-test was performed on two homoscedastic samples and the t-test was performed on two heteroscedastic samples (one-sided distribution). Incidentally, the results indicated in Tables 7 and 8 are numerical values obtained after Bonferroni correction. Assuming that the significance level is 5%, the results indicated in Tables 7 and 8 indicate that there is a statistical significant difference in R, Rb, peak value to Rb/α, slope to peak, and peak value of α between the weak sheet and the normal sheet, and also there is a statistical significant difference in R, peak of Rb, and slope to peak between the weak sheet and the detached sheet. However, there is no statistical significant difference between the normal sheet and the detached sheet. For further examination, a comparison was made between the numerical value of the group of weak sheet and the numerical value of the two groups (combined together) of normal sheet and detached sheet. Then, another comparison was made between the numerical value of the group of normal sheet and the numerical value of the group of detached sheet, with the group of normal sheet and the group of detached sheet combined together. It was found that there is a statistical significant difference between the group of weak sheet and the two groups (combined together) of normal sheet and detached sheet in R, Rb, α, peak value of Rb/α, time to peak of Rb and Rb/α, and slope to peak of R, Rb, and Rb/α. Moreover, there is a statistical significant difference between the group of normal sheet and the group of detached sheet in the peak value of R.

The foregoing findings suggest that the cells capable of growing into a weak sheet, normal sheet, or detached sheet can be discriminated by using as the index the peak value, time to peak, and slope to peak of such parameters as R, Rb, α, and Rb/α. In order to verify the foregoing assumption, the reference values (indicated in Tables 11 and 12) were established for the peak value, time to peak, and slope to peak for the respective parameters. In addition, an investigation was made to see whether the foregoing discrimination is possible. The results are indicated in Tables 13 and 14.

TABLE 11

Reference values for peak values of R and Rb, time to peak, and slope to peak

| | R | | | Rb | | |
|---|---|---|---|---|---|---|
| | Peak value (Ω) | Time to peak (h) | Slope to peak (Ω/h) | Peak value (Ω · $cm^2$) | Time to peak (h) | Slope to peak (Ω · $cm^2$/h) |
| Weak sheet | Smaller than 550 | Longer than 6 | Smaller than 150 | Smaller than 1.5 | Longer than 6 | Smaller than 0.3 |
| Normal sheet | 550 to 1000 | Equal to or shorter than 6 | 150 to 350 | 1.5 to 2.5 | Equal to or shorter than 6 | Equal to or larger than 0.3 |
| Detached sheet | Larger than 1000 | | Larger than 350 | Larger than 2.5 | Shorter than 2 | Larger than 0.5 |

TABLE 12

Reference values for peak values of α and Rb/α, time to peak, and slope to peak

| | α | | | Rb/α | | |
|---|---|---|---|---|---|---|
| | Peak value (cm · $Ω^{0.5}$) | Time to peak (h) | Slope to peak (cm · $Ω^{0.5}$/h) | Peak value (cm · $Ω^{0.5}$) | Time to peak (h) | Slope to peak (cm · $Ω^{0.5}$/h) |
| Weak sheet | Smaller than 4.5 | Longer than 3.5 | Smaller than 1.5 | Smaller than 0.3 | Longer than 6 | Smaller than 0.05 |
| Normal sheet | Equal to or larger than 4.5 | Equal to or shorter than 3.5 | Equal to or larger than 1.5 | 0.3 to 0.55 | 2 to 6 | 0.05 to 0.5 |
| Detached sheet | | | | Larger than 0.55 | Shorter than 2 | Larger than 0.5 |

TABLE 13

Ratio of correspondence with reference values for each group (Part 1)

| | R | | | Rb | | |
|---|---|---|---|---|---|---|
| Reference values | Peak value | Time to peak | Slope to peak | Peak value | Time to peak | Slope to peak |
| Group of weak sheet | | | | | | |
| Weak sheet | 100% | 18% | 91% | 100% | 45% | 91% |
| Normal sheet | 0% | 82% | 9% | 0% | 55% | 9% |
| Detached sheet | 0% | | 0% | 0% | | |
| Group of normal sheet | | | | | | |
| Weak sheet | 11% | 0% | 17% | 22% | 0% | 6% |
| Normal sheet | 61% | 100% | 62% | 50% | 100% | 94% |
| Detached sheet | 28% | | 22% | 28% | | |
| Group of detached sheet | | | | | | |
| Weak sheet | 0% | 0% | 0% | 0% | 0% | 0% |
| Normal sheet | 0% | 100% | 33% | 33% | 100% | 100% |
| Detached sheet | 100% | | 67% | 67% | | |

TABLE 14

Ratio of correspondence with reference values for each group (Part 2)

| Reference values | α | | | Rb/α | | |
|---|---|---|---|---|---|---|
| | Peak value | Time to peak | Slope to peak | Peak value | Time to peak | Slope to peak |
| Group of weak sheet | | | | | | |
| Weak sheet | 73% | 36% | 55% | 55% | 64% | 64% |
| Normal sheet | 27% | 64% | 45% | 45% | 36% | 36% |
| Detached sheet | | | | 0% | 0% | 0% |
| Group of normal sheet | | | | | | |
| Weak sheet | 6% | 17% | 17% | 17% | 11% | 11% |
| Normal sheet | 94% | 83% | 83% | 83% | 89% | 89% |
| Detached sheet | | | | 0% | 0% | 0% |
| Group of detached sheet | | | | | | |
| Weak sheet | 33% | 0% | 0% | 33% | 0% | 0% |
| Normal sheet | 67% | 100% | 100% | 0% | 67% | 67% |
| Detached sheet | | | | 67% | 33% | 33% |

It is considered that the reference values are extremely useful if they have 100% or 0% for the group of cells belonging to specific classes.

The present invention has distinguishing features as described in this specification, and such features will be used in various forms of combination. Any embodiment derived from such combination will be included in the scope of the present invention regardless of whether or not such embodiments are explicitly described in this specification. Those who are skilled in the art are aware that the present invention can be variously modified within the scope thereof, and such modifications and equivalents thereof are also within the scope of the present invention. It should be understood, therefore, that the embodiments disclosed in this specification are mere examples and they are not intended to restrict the scope of the present invention.

What is claimed is:

1. A method for evaluating the ability of cells to grow into a sheet, comprising:
   examining cell cultures growing into a sheet to determine, using a measuring apparatus, one or more numerical values relating to impedance and/or electrical resistance of the cell cultures growing into a sheet, the numerical values being parameters selected from the group consisting of electrical resistance, capacitance, Rb, α, Rb/α, and Cm and peak values, times to peak, and slopes to peak of the parameters;
   comparing one or more of the determined numerical values with one or more reference values;
   judging, based on the results of comparing, the ability of cells to grow into a sheet; and
   controlling a process for producing the sheet-shaped cell culture based on the result of the judging,
   wherein cells are judged to be low in ability to grow into a sheet if
      the peak value of the electrical resistance, the peak value of Rb, or the slope to peak of Rb determined is equal to or smaller than the one or more reference values, or
      the time to peak of the electrical resistance or the time to peak of Rb determined is equal to or larger than the one or more reference values.

2. The method defined in claim 1, wherein the determination of impedance and/or electrical resistance is performed periodically.

3. The method defined in claim 1, wherein the determination of one or more numerical values further includes determination of voltage phase relative to current phase.

4. The method defined in claim 1, wherein the determining of the one or more numerical values includes determining the one or more numerical values relating to the impedance of the cell cultures growing into a sheet, and the determination of impedance is performed at two or more frequencies.

5. The method defined in claim 1, wherein the cells are judged to be low in ability to grow into a sheet if the determined electrical resistance is equal to or smaller than the reference value.

6. The method defined in claim 1, wherein cells are judged to be low in ability to grow into a sheet if the determined values of Rb, α, and Rb/α are equal to or smaller than the reference values.

7. The method defined in claim 1, wherein cells are judged to be adequate or excessive in ability to grow into a sheet if the determined values of Rb, α, and Rb/α are equal to or larger than the reference values.

8. The method defined in claim 1, wherein cells are judged to be adequate in ability to grow into a sheet if the numerical values selected from a group consisting of the time to peak of electrical resistance and the time to peak of Rb are equal to or smaller than the reference values and the numerical values selected from a group consisting of the peak value of Rb/α and the slope to peak of Rb/α are equal to or smaller than the reference values, and/or if the numerical values selected from the group consisting of the time to peak of electrical resistance and the time to peak of Rb are equal to or smaller than the reference values and the time to peak of Rb/α is equal to or longer than the reference value.

9. The method defined in claim 1, wherein cells are judged to have excessive ability to grow into a sheet if the numerical values selected from a group consisting of the peak value of Rb/α and the slope to peak of Rb/α are equal to or larger than the reference values, and/or if the time to peak of Rb/α is equal to or shorter than the reference value.

10. A method for producing a sheet-shaped cell culture, comprising:
   performing sheet-forming cultivation to obtain one or more cell cultures growing into a sheet;
   examining the one or more cell cultures growing into a sheet to determine one or more numerical values relating to impedance and/or electrical resistance of the cell cultures growing into a sheet, the numerical values being parameters selected from the group consisting of electrical resistance, capacitance, Rb, α, Rb/α, and Cm and peak values, times to peak, and slopes to peak of the parameters;
   comparing one or more of the determined numerical values with one or more reference values;
   judging, based on the results of the comparing, the ability of cells to grow into a sheet; and
   controlling, based on the result of the judging, a process of producing the sheet-shaped cell culture,
   wherein cells are judged to be low in ability to grow into a sheet if
      the peak value of the electrical resistance, the peak value of Rb, or the slope to peak of Rb determined is equal to or smaller than the one or more reference values, or the time to peak of the electrical resistance or the time to peak of Rb determined is equal to or larger than the one or more reference values.

11. The method defined in claim 10, wherein the determination of impedance and/or electrical resistance is performed periodically.

12. The method defined in claim 10, wherein the determination of the one or more numerical values further includes determination of voltage phase relative to current phase.

13. The method defined in claim 10, wherein the determining of the one or more numerical values includes determining the one or more numerical values relating to the impedance of the cell cultures growing into a sheet, and the determination of the impedance is performed at two or more frequencies.

14. A method for producing a sheet-shaped cell culture, comprising:
  performing sheet-forming cultivation to obtain one or more cell cultures growing into the sheet-shaped cell culture;
  determining impedance and/or electrical resistance of the one or more cell cultures growing into the sheet-shaped cell culture to obtain one or more numerical values relating to the determined impedance and/or electrical resistance, the one or more obtained numerical values being parameters selected from the group consisting of electrical resistance, capacitance, Rb, $\alpha$, Rb/$\alpha$, and Cm and peak values, times to peak, and slopes to peak of the parameters;
  comparing one or more of the obtained numerical values with one or more reference values; and
  judging, based on the results of the comparing, the ability of the cell cultures to grow into a sheet, wherein the cells are judged to be low in ability to grow into the sheet if the peak value of electrical resistance, the peak value of Rb, or the slope to peak of Rb determined is equal to or smaller than the one or more reference values, or the time to peak of electrical resistance or the time to peak of Rb determined is equal to or larger than the one or more reference values.

15. The method defined in claim 14, wherein the determination of impedance and/or electrical resistance is performed periodically.

16. The method defined in claim 14, wherein the determination of the one or more numerical values further includes determination of voltage phase relative to current phase.

17. The method defined in claim 14, wherein the determining of the one or more numerical values includes determining the one or more numerical values relating to the impedance of the cell cultures growing into a sheet, and the determining of the impedance is performed at two or more frequencies.

18. The method defined in claim 14, wherein cells are judged to be low in ability to grow into a sheet if the determined electrical resistance is equal to or smaller than the reference value.

19. The method defined in claim 14, wherein cells are judged to be low in ability to grow into a sheet if the determined values of Rb, $\alpha$, and Rb/$\alpha$ are equal to or smaller than the reference values.

20. The method defined in claim 14, wherein cells are judged to be adequate or excessive in ability to grow into a sheet if the values of Rb, $\alpha$, and Rb/$\alpha$ determined are equal to or larger than the reference values.

* * * * *